(12) United States Patent
Kidmose et al.

(10) Patent No.: US 12,257,057 B2
(45) Date of Patent: Mar. 25, 2025

(54) ELECTRODE FOR DETECTING BIOELECTRICAL SIGNALS

(71) Applicant: T&W Engineering A/S, Lynge (DK)

(72) Inventors: Preben Kidmose, Maarslet (DK); Mike Lind Rank, Farum (DK); Hans Olaf Toft, Copenhagen (DK); Mikael Andersen, Allerod (DK); Simon Lind Kappel, Herning (DK)

(73) Assignee: T&W Engineering A/S, Lynge (DK)

( * ) Notice: Subject to any disclaimer, the term of this patent is extended or adjusted under 35 U.S.C. 154(b) by 1012 days.

(21) Appl. No.: 16/975,586

(22) PCT Filed: Feb. 26, 2019

(86) PCT No.: PCT/EP2019/054681
§ 371 (c)(1),
(2) Date: Aug. 25, 2020

(87) PCT Pub. No.: WO2019/162518
PCT Pub. Date: Aug. 29, 2019

(65) Prior Publication Data
US 2022/0031217 A1 Feb. 3, 2022

Related U.S. Application Data

(60) Provisional application No. 62/635,237, filed on Feb. 26, 2018.

(51) Int. Cl.
*A61B 5/291* (2021.01)
*A61B 5/00* (2006.01)
(Continued)

(52) U.S. Cl.
CPC ............. *A61B 5/291* (2021.01); *A61B 5/263* (2021.01); *A61B 5/4094* (2013.01);
(Continued)

(58) Field of Classification Search
CPC ....... A61B 5/277; A61B 5/291; A61B 5/6815; A61B 5/6817; A61B 2562/0214; A61B 5/263–27; A61B 5/25–297
See application file for complete search history.

(56) References Cited

U.S. PATENT DOCUMENTS

| 9,415,220 B1* | 8/2016 | Spinelli | A61N 1/36036 |
| 2011/0125001 A1* | 5/2011 | Fang | A61B 5/685 |
| | | | 156/60 |

(Continued)

FOREIGN PATENT DOCUMENTS

| CN | 106419906 A * | 2/2017 | A61B 5/04 |
| GB | 1147442 A | 4/1969 | |

(Continued)

OTHER PUBLICATIONS

N.S. Dias et al., "New dry electrodes based on iridium oxide (IrO) for non-invasive biopotential recordings and stimulation", Sensors and Actuators A: Physical, Nov. 1, 2010, pp. 28-34, vol. 164, No. 1-2.

(Continued)

*Primary Examiner* — Daniel L Cerioni
*Assistant Examiner* — Raymond P Dulman
(74) *Attorney, Agent, or Firm* — Sughrue Mion, PLLC

(57) ABSTRACT

The invention relates to an electrode for detecting a bioelectrical signal, for example EEG, on a skin surface. The electrode comprises a coating comprising iridium oxide, where the coating has a nanostructured surface pattern providing for a capillary and hydrophilic effect when in use.

11 Claims, 17 Drawing Sheets

(51) Int. Cl.
*A61B 5/263* (2021.01)
*H04R 25/00* (2006.01)

(52) U.S. Cl.
CPC ......... *A61B 5/6817* (2013.01); *H04R 25/658* (2013.01); *A61B 2562/0214* (2013.01); *A61B 2562/125* (2013.01)

(56) References Cited

U.S. PATENT DOCUMENTS

| | | | | |
|---|---|---|---|---|
| 2016/0120472 A1* | 5/2016 | Kub | ...................... | C23C 16/405 216/13 |
| 2018/0168514 A1* | 6/2018 | Matsumoto | .......... | A61B 5/6843 |

FOREIGN PATENT DOCUMENTS

| GB | 1195871 A | 6/1970 | | |
|---|---|---|---|---|
| WO | 2005/033367 A1 | 4/2005 | | |
| WO | 2006/047874 A1 | 5/2006 | | |
| WO | 2006/080926 A1 | 8/2006 | | |
| WO | 2007/047667 A2 | 4/2007 | | |
| WO | WO 2009015627 | * | 2/2009 | .......... A61F 2/7812 |
| WO | 2011/000383 A1 | 1/2011 | | |
| WO | 2017/054875 A1 | 4/2017 | | |

OTHER PUBLICATIONS

S. Yamagiwa et al., "Layer-by-layer nanoassembly of iridium oxide/platinum-black for low impedance, high charge injecting microelectrode applications", Micro Electro Mechanical Systems(MEMS), 2012 IEEE 25th International Conference on, IEEE, Jan. 29, 2012, pp. 184-187.
International Search Report for PCT/EP2019/054681 dated Jun. 4, 2019 [PCT/ISA/210].
Written Opinion for PCT/EP2019/054681 dated Jun. 4, 2019 [PCT/ISA/237].

* cited by examiner

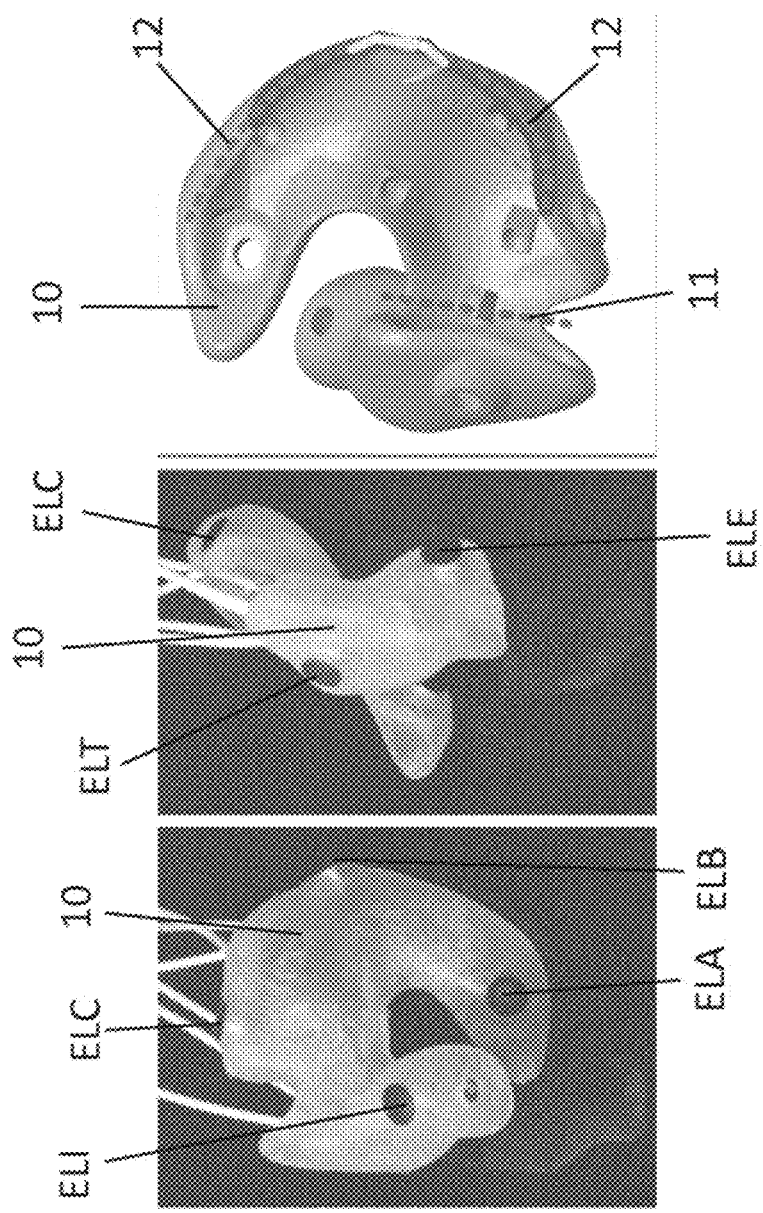

ELECTRODE FOR DETECTING BIOELECTRICAL SIGNALS

CROSS REFERENCE TO RELATED APPLICATIONS

This application is a National Stage of International Application No. PCT/EP2019/054681 filed Feb. 26, 2019, claiming priority based on U.S. Provisional Application No. 62/635,237 filed Feb. 26, 2018.

The invention relates to an electrode for detecting bioelectrical signals, a method for manufacturing an electrode for detecting bioelectrical signals and an ear device comprising such electrode.

BACKGROUND OF THE INVENTION

Bioelectrical signals are here understood to be electrical potential differences originating from a living body. Well-known examples are Electrocardiogram (ECG) signals and Electroencephalogram (EEG) signals. An ear component for detecting bioelectrical signals at the ear is often made for the detection of EEG signals, but could also be applied for detecting other bioelectrical signals such as ECG, electrooculography (EOG), or muscular activity.

EEG signals are electrical signals generated by a person's brain activity. In recent years, EEG monitoring systems, that may be carried or worn continuously by a person to be monitored, have been devised. A goal is to have personal wearable EEG monitors, which can be carried without causing more inconvenience than glasses or a modern small hearing aid, even when carried over several months or years.

Such EEG monitors may be applied for different purposes. One example is surveillance of a condition of a person and e.g. for providing an alarm or information in case predetermined conditions are met. The monitor may also be applied for collection of data, e.g. for diagnostic purposes or for research use. Examples of applications are for surveillance of persons having diabetes or epilepsy. Another example is as input to the control or adjustment of a hearing aid.

Moreover, in recent years there has been a lot of activities within transcranial neuro-stimulation (e.g. tDCS and tACS). Here, electrodes are used for recording electrical signals, but also for neuro-stimulation. Another application could be measurement of galvanic skin-responses (GSR).

Furthermore, electric potentials originating from neural activity in the cranial nerves and in the brain stem may also be measured with ear devices. This is e.g. relevant in assessment of hearing loss, where it is common to measure responses from the cranial nerve (cranial nerve 8) and from the brain stem (as in auditory brain stem responses). But it may also be relevant to measure responses from or stimulation of e.g. the vagus nerve (cranial nerve 10) which have branches out in the external ear. This may e.g. be of relevance in epilepsies.

Measuring the EEG signal in the ear canal is known from WO 2011/000383 A1 disclosing an ear plug with EEG electrodes where the ear plug shape is individually matched or customized to the user's ear canal.

WO 2007/047667 A2 discloses an ear plug made from a compressible material and provided with EEG ear canal electrodes. External ear electrodes are arranged on a measurement device, which is worn behind the ear. Thereby, the housing of the measurement device is shaped/customized to the curved contour of the ear of an individual.

It is generally known, particularly within medical science, to measure brain waves by placing electrodes on the scalp of a subject, whose brain waves it is desired to measure, processing, and interpreting the measured brain waves using suitable equipment. Typically, such equipment is an electroencephalograph, by means of which a so-called electroencephalogram (EEG) may be achieved. Such an EEG provides a measurement and recording of electrical activity in a subject's brain by measuring the electric potential generated on the surface of the subject's scalp by postsynaptic currents in the subject's brain. Within medical science EEG's are used for various diagnostic purposes.

A system for such a use is known from WO-A1-2006/047874, which describes measurement of brain waves by use of electrodes placed in connection with at least one of the ears of the subject, i.e. placed on an outer ear part or placed in the ear canal. The measurements are used particularly for detecting the onset of an epileptic seizure. WO-A1-2006/047874 also describes the use of electrodes in pairs as detection and reference electrodes respectively, such a setup being well known in the field of electroencephalography.

The known systems for measuring brain waves are generally complicated to use and require qualified personnel to operate, or require surgery to place the electrodes, and even when placed properly, there are still large variations in the recorded EEG, due to variations in the electrical coupling. Conventional EEG recording systems have relatively large power consumption. Despite the potential in continuous surveillance of users' EEG response in many different areas of medicine and physical science, the systems known are largely confined to laboratory use.

Conventional laboratory EEG recordings are typically performed with wet Ag/AgCl electrodes, where an electrode gel is applied between the electrode and skin. The electrode gel is usually a solution with ionic concentrations higher than the extracellular fluid in the human body. The electrode gel improves the ion transport between the skin and the electrode. Even when using a conductive electrode gel, the electrical path may still be poor, due to the moist, dirt and hair at the skin of the user. This is especially a problem, when the monitor is to be used for longer periods of time, where the user is active and is subjected to non-laboratory environment, i.e. dirt, moist etc. One of the arguments for the extensive use of Ag/AgCl electrodes is that the potential over the electrode-skin interface stabilizes within a few minutes, enabling low noise recordings shortly after application of the electrode. For a lab environment, the application of gel between the electrode and skin is normally not a problem. However, the need for a conductive gel makes such systems rather unattractive to use in public, because the conductive gel is greasy and not confined to the area covered by the electrode. Furthermore, the conductive gel is likely to short-circuit the electrodes, if they are placed in close proximity of each other, therefore these known systems needs spacing between the electrodes, leading to a large and bulky device for monitoring the EEG.

The present invention therefore aims at providing an electrode for detecting bioelectrical signals for long-term, continuous, non-invasive monitoring, which electrode may be used in an uncomplicated way in everyday life outside clinical and laboratory environment, while obtaining high quality bioelectrical signal responses from a user.

SUMMARY OF THE INVENTION

According to a first aspect of the invention, this object is achieved by providing an electrode for detecting a bioelectrical signal on a skin surface, where the electrode comprises a skin contact part, a substrate made of a metal, and a coating comprising iridium oxide. The coating covers at least part of the skin contact part of the electrode, and the coating has a nanostructured surface pattern.

In the context of this application, nanostructured means three dimensional microstructures at micrometer and/or nanometer scale.

The nanostructured surface pattern comprises multiple ridges substantially evenly distributed over the skin contact part of the electrode which is covered by the coating. The multiple ridges form a grid of intersecting ridges.

The nanostructured surface pattern provides a capillary effect, making the part of the skin contact part, which is covered by the coating, hydrophilic when in use on the skin. This hydrophilic property of the electrode enhances the efficiency of the electrode significantly yielding similar results as known wet electrodes while at the same time providing the user with the ease of use of a dry electrode in that it is not necessary to rinse off the skin nor applying an electrode gel prior to placing the electrode as would be the case with wet electrodes. The test results from a comparative study of electrodes according to the invention and conventional wet Ag electrodes are included at the end of the patent specification.

Usually EEG electrodes are flat surfaced as they rely on gel for their skin contact. For a dry surface electrode, it is essential that the electrode surface is in direct contact with the skin as the electrode impedance is inversely proportional to its contact surface area. For a flat surfaced electrode, this ideally means that it must be placed on a planar skin surface. Such planar skin surfaces do not exist on humans, but in reality, almost planar surfaces will do, as the skin can be somewhat compressed by the electrode. When the electrode is for use in the ear, the skin surface cannot be considered planar unless the electrode diameter is very small. Otherwise it will only be in contact with the skin at its perimeter.

Ideally, a dry surface electrode for use in the ear, is shaped so that it fits the curvature of that particular ear. A non-customized ear electrode should mimic the generalized features of a human ear, implying that the electrode surface should be dome shaped or otherwise curved with a curvature radius matching the curvature found in the features of a human ear. The curvature of the electrode surface does not need to match the features of the ear exactly, as it can rely on some skin compression to compensate for differences. However, if the curvature radius becomes smaller than what can be absorbed by skin compression, the electrode will lose skin contact at its perimeter. If the curvature radius becomes larger than what can be absorbed by skin compression, it will lose skin contact in its center. Due to the compressibility of the skin, there will be an interval of curvature radii, that ensures that the entire surface, or at least a major part thereof, of the electrode is in contact with the skin.

In a preferred embodiment, the skin contact part of the electrode comprises a curved surface adapted for facing a skin surface of a user, when the electrode is in use.

The electrode has a base diameter D. In a preferred embodiment, the base diameter D is between 1.0 and 5.0 mm, more preferred 1.5-3.5 mm, even more preferred 2.0-3.0 mm, and with a most preferred base diameter D of 2.6 mm.

In a preferred embodiment, the surface of the skin contact part of the electrode which surface is adapted to contact the skin of a user, when the electrode is in use, is curved with a curvature radius R of between 2 and 7 mm. A more preferred curvature radius R is between 2.1 and 5 mm, most preferred between 2.2 and 4 mm.

Iridium oxide has proven to be surprisingly suitable for the coating of the electrode according to the invention, as test results show, both in terms of hydrophilic properties and efficiency compared to wet Ag electrodes as shown in the comparative study in the last part of the description of this patent application.

In the context of this patent application, hydrophilic is defined as when the contact angle of a drop of liquid on a plane surface is below 90°. For the part of the skin contact part, which is covered by the coating, the hydrophilic properties have been documented by application of water and n-Hexadecane, respectively, on the electrode.

| Water | | |
| --- | --- | --- |
| | Start | After 10 minutes |
| Test 1 | 59.6° | 34.4° |
| Test 2 | 54.3° | 33.6° |

| n-Hexadecane | | |
| --- | --- | --- |
| | Start | After 10 minutes |
| Test 3 | 26.7° | — |
| Test 4 | 26.1° | 22.0° |

Measurements were made using Contact Angle System OCA 20 S/N O02E0412F7A6 (DataPhysics Instruments GmbH, Filderstadt, Germany).

In a preferred embodiment the substrate of the electrode is made of titanium. Titanium is a stable and biocompatible material which makes it highly suitable for an electrode adapted for detecting a bioelectrical signal on a skin surface of a user, especially when the electrodes are used for longer periods of time, where the user is active and is subjected to non-laboratory environment.

Other materials for the substrate can be used, e.g. Ag, silver. Biocompatible materials are preferred.

The substrate may preferably be in the shape of a pin.

The coating may comprise different materials, for example the materials for coatings disclosed in GB1147442A and GB1195871A, both of which documents are hereby incorporated by reference.

In a preferred embodiment, the coating of the electrode according to the invention comprises additives chosen from the group of tantalum, titanium, platinum and ruthenium. These materials are biocompatible. One of the advantages of these materials is that they disturb a crystallization process of the iridium oxide coating making the coating porous. The coating has a nanostructured surface pattern and a porous surface which provides a capillary effect, making the part of the skin contact part, which is covered by the coating, hydrophilic when in use on the skin. This hydrophilic property of the electrode enhances the efficiency of the electrode significantly, yielding similar reliability as known wet electrodes while at the same time overcoming some of the drawbacks of known wet electrodes.

According to a second aspect of the invention, a method for manufacturing an electrode for detecting a bioelectrical signal on a skin surface is provided. The method comprises the steps of providing a substrate made from a metal, etching at least part of the substrate to prepare for coating, coating the etched part of the substrate with a coating composition comprising an iridium compound, and heating the coated substrate at a temperature of between 400 and 600 degrees Celsius. By performing these steps, an electrode comprising an iridium oxide coating with a nanostructured surface pattern is provided.

The nanostructured surface pattern provides a capillary effect, making the part of the skin contact part, which is covered by the coating, hydrophilic when in use on the skin. This hydrophilic property of the electrode enhances the efficiency of the electrode significantly, yielding similar reliability as known wet electrodes while at the same time overcoming some of the drawbacks of known wet electrodes. Thus, an electrode is provided where it is not necessary to rinse off the skin nor applying an electrode gel prior to placing the electrode as would be the case with wet electrodes. Thus, the electrode can be used as a dry electrode with all the benefits and advantages in easy handling and suitable for use over longer periods of time outside a laboratory environment. The test results from a comparative study of electrodes according to the invention and conventional wet Ag electrodes are included at the end of the patent specification.

The coating of the electrode according to the invention comprises iridium oxide. Iridium oxide has proven to be surprisingly suitable for the coating of the electrode according to the invention, as test results show, both in terms of hydrophilic properties and efficiency compared to wet Ag electrodes as shown in the comparative study in the last part of the description of this patent application.

The etching step can be performed by use of any suitable etching or passivating agent. Examples of such etching or passivating agents include hydrofluoric acid, nitric acid or oxalic acid.

The steps of coating and heating can be repeated one or more times to obtain a coating of increased thickness, i.e. comprising a larger amount of iridium oxide per $m^2$ measured on the area of the electrode covered by the coating.

A preferred amount of iridium oxide is 12 $g/m^2$ measured on the area of the electrode covered by the coating.

In a preferred embodiment of the second aspect of the invention, the coated substrate is subjecting to heating in the heating step for 3 to 19 minutes, more preferred 6 to 16 minutes, most preferred 9 to 13 minutes.

In a preferred embodiment of the second aspect of the invention, the method further comprises a drying step after the coating step and prior to the heating step.

The steps of coating, drying and heating can be repeated one or more times to obtain a coating of increased thickness, i.e. comprising a larger amount of iridium oxide per $m^2$.

A preferred amount of iridium oxide is 12 $g/m^2$ measured on the area of the electrode covered by the coating.

In an embodiment of the second aspect of the invention, the drying step is performed at 100-120 degrees Celsius, more preferred at approximately 105 degrees Celsius.

In a preferred embodiment of the second aspect of the invention, the temperature of the heating step is 500-550 degrees Celsius, more preferred approximately 525 degrees Celsius.

In a preferred embodiment of the second aspect of the invention, the provided substrate is made of titanium. Titanium is a stable and biocompatible material which makes it highly suitable for an electrode adapted for detecting a bioelectrical signal on a skin surface of a user, especially when the electrodes are used for longer periods of time, where the user is active and is subjected to non-laboratory environment.

Other materials for the substrate can be used, e.g. Ag, silver. Biocompatible materials are preferred.

Preferably, the iridium compound is provided in the form of a liquid composition.

In a preferred embodiment of the second aspect of the invention, the iridium compound is iridium chloride.

The coating may comprise different materials, for example the materials for coatings disclosed in GB1147442A and GB1195871A, both of which documents are hereby incorporated by reference.

In a preferred embodiment of the second aspect of the invention, the coating of the electrode according to the invention comprises additives chosen from the group of tantalum, titanium, platinum, and ruthenium. The advantages of these materials are as stated above under the first aspect of the invention.

According to a third aspect of the invention, an electrode obtainable by the method of the second aspect of the invention, is provided.

According to a fourth aspect of the invention, an ear device for arrangement at an ear of a person, the ear device comprising at least two electrodes according to the first or third aspect of the invention, the ear device being adapted for detecting a bioelectrical signal from a skin surface when the ear device is arranged at the ear of the person. The ear device further comprises an outer surface and an electronic module comprising power supply mean. The electrodes are provided with a skin contact part arranged on the outer surface of the ear device The power supply means may be a battery, a rechargeable battery or a fuel cell, preferably of the type Direct Methanol Fuel Cell, DMFC.

The electronic module may comprise a controller (CPU).

The electronic module may comprise a memory means.

The electronic module may comprise a communication means, for example Bluetooth connection means or WiFi connection means, for example WLAN connection means.

The electronic module may comprise a real-time clock, RTC.

The electronic module may comprise a loudspeaker means.

The ear device may be made of a flexible material that adapts to the shape of an ear canal.

The electrodes may be fixed to an inner non-flexible part of the ear device, covered with an outer flexible part, which conforms to the shape of the ear canal.

In one embodiment according to the fourth aspect of the invention, the electrodes are distributed evenly over the circumference of the ear device.

In the context of the present invention, an electrode is meant to be a pseudocapacitive electrode. A pseudocapacitive electrode is a material with the electrochemical signature of a polarizable (capacitive) electrode, but where charge is not stored electrostatically. Instead charge transfer in a pseudocapacitive interface is due to fast and reversible faradaic redox reactions on the surface of the electrode. Thus, pseudocapacitance originate from electron charge-transfer through changes in the oxidation state of the electrode material, and corresponding insertion (electrosorption) of ions from the electrolyte, which has pervaded the double-layer. This means that no ions of the electrode material are released to the electrolyte.

For some electrode materials, pseudocapacitance is the dominating method of charge transfer and the pseudocapacitance is much higher than the double-layer capacitance Double-layer capacitance is the storing of electrical energy by means of the electrical double layer effect. The double-layer capacitance is formed in the interface between the electrode and the electrolyte, in this case the moistened skin. This is the case for coatings like ruthenium oxide ($RuO_2$) and iridium-oxide ($IrO_2$).

BRIEF DESCRIPTION OF THE DRAWINGS

Embodiments of the invention will now be described in more detail with reference to figures, in which FIGS. 6A and 6B show soft-earpiece for a left ear, with electrodes inserted in positions A, B, C, T, E, and I, FIG. 6C is a representation of an earpiece, with indication of the means used to improve skin contact for dry-contact electrode recordings.

DETAILED DESCRIPTION OF THE INVENTION

Figure 1A:
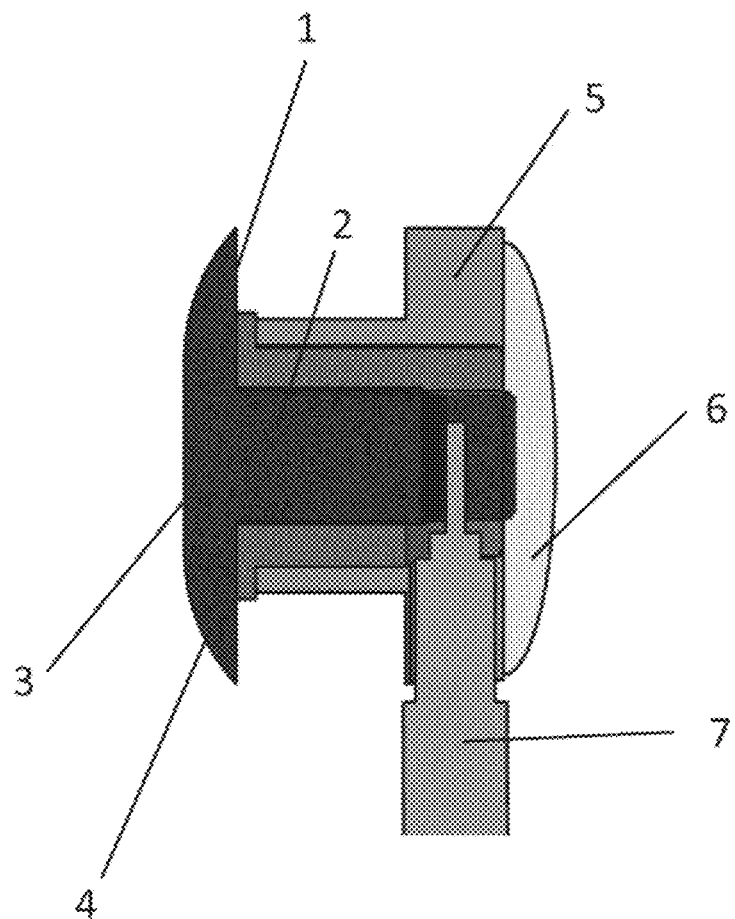
FIG. 1A is a cross-sectional, schematic drawing of an electrode according to the invention inserted in an electrode housing.

FIG. 1A shows a cross-section of an embodiment of an electrode 1 according to the first aspect of the invention. The electrode 1 comprises a substrate 2 of titanium, the substrate having a skin contact part 4 covered by a coating 3 comprising iridium oxide. The electrode 1 is inserted in an electrode housing 5 comprising a sealing means 6 on part of the electrode which is opposite of the skin contact part 4. The sealing means 6 can be made of any suitable material, for example epoxy. The electrode 1 comprises connection means 7 in the form of a coax cable.

The sealing means 6 seals part of the electrode 1 located in the electrode housing 5 against the outside environment surrounding the electrode housing 5. In one embodiment the sealing means 6 is made of metal. In a preferred embodiment the sealing means 6 provides a substantially waterproof seal between the sealing means 6 and the electrode housing 5.

For dry-contact electrodes, the electrolyte in the electrode-skin interface will primarily be formed by perspiration from the skin. Thus, the amount of electrolyte will typically be quite limited, and the double-layer in the electrode-skin interface can easily be disturbed by motion. Disturbance of the double-layer will change the half-cell potential and capacitance of the electrode-skin interface. In addition, motion will alter the geometrical area between the electrode and skin, which also change the capacitance of the interface. These aspects contribute to a higher and more varying impedance of the electrode-skin interface for dry-contact electrodes, compared to wet electrodes. Thus, in order to measure EEG with dry-contact electrodes, the electronic instrumentation must be designed to accommodate these higher and more varying impedances. The impedance of the electrode-skin interface can often be reduced by increasing the surface area of the electrode. However, there is typically a trade-off between the size of the electrodes and the distance between the electrodes. In order to achieve a better trade-off, a nanostructured surface coating can be utilized to increase the surface area of the electrode without increasing the size of the electrode.

Although the electrodes according to the invention are suitable for use without the application of a conductive gel, i.e. as dry electrodes, electrodes and the ear device according to the invention may be used with the application of a conductive gel.

Figure 1B:
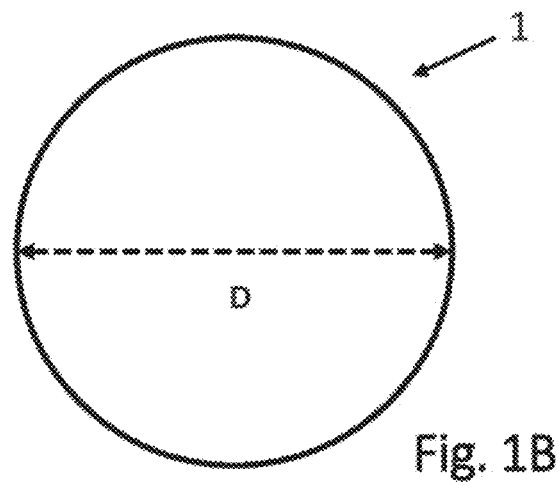
FIG. 1B is a schematic top view of an electrode according to the invention.

FIG. 1B is a schematic top view of an electrode 1. D denotes a base diameter of the electrode.

Figure 1C:
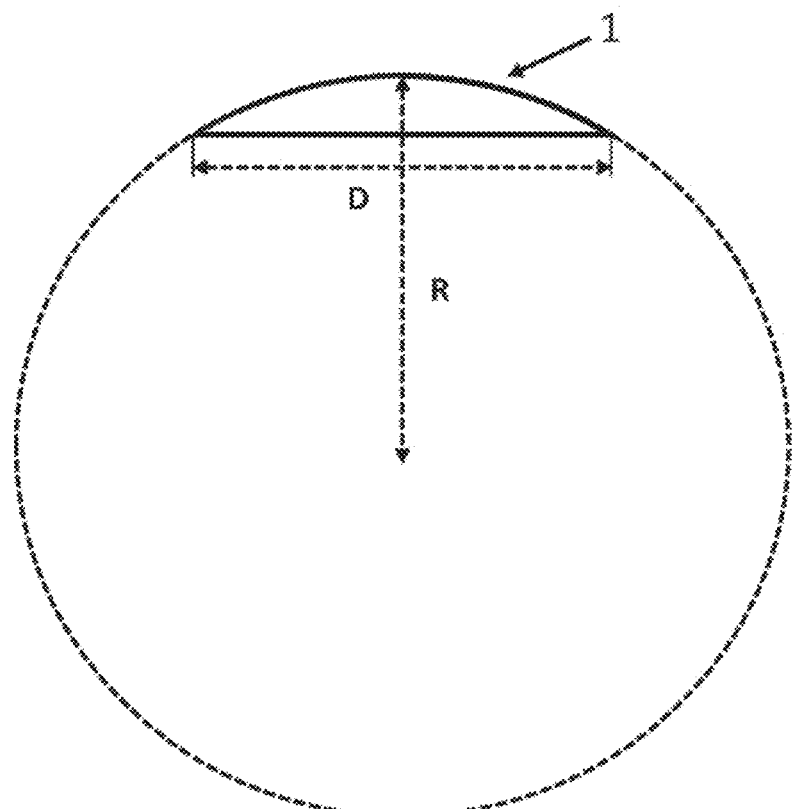
FIG. 1C is a schematic side view of an electrode according to the invention.

FIG. 1C is a schematic side view of an electrode 1. D denotes a base diameter of the electrode and R a curvature radius of a dome of the electrode. The dotted circle indicates the circle which has the curvature radius R. Thus, the relationship between D and R can be seen in the figure. If R is much larger than D, the dome, i.e. the surface of the electrode adapted to contact the skin of a user, is substantially flat. In this context, much larger could be when R is five times larger than D. If R=D/2 the dome is a half sphere.

To obtain an electrode with a preferred curvature radius, the following formula is used:

$$R = \text{beta} * D/2$$

A value of beta in the interval of 1-20 comprises all practical solutions for electrodes that suits the purpose of the invention. A preferred interval is a beta of 1.2 to 9, more preferred 1.4-3.6 and most preferred a beta of approximately 1.8.

Figure 1D:
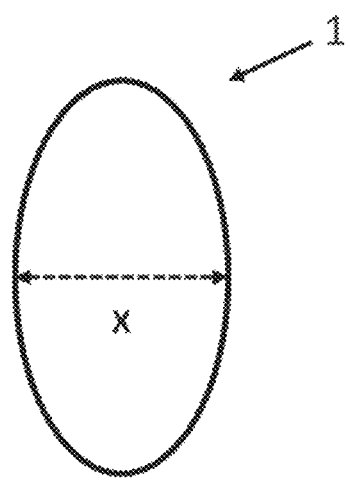
FIG. 1D is a schematic top view of an electrode according to the invention.

FIG. 1D is a schematic top view of an embodiment of an electrode 1 according to the invention. In this embodiment, the electrode 1 is of an elliptical shape. In such a case, the value of D is set at two times the minor axis X of the elliptical electrode as seen in the figure, a top view. For other shapes, the value of D is set at two times the smallest axis X as seen from a top view similar to that of FIG. 1D.

Figure 2:
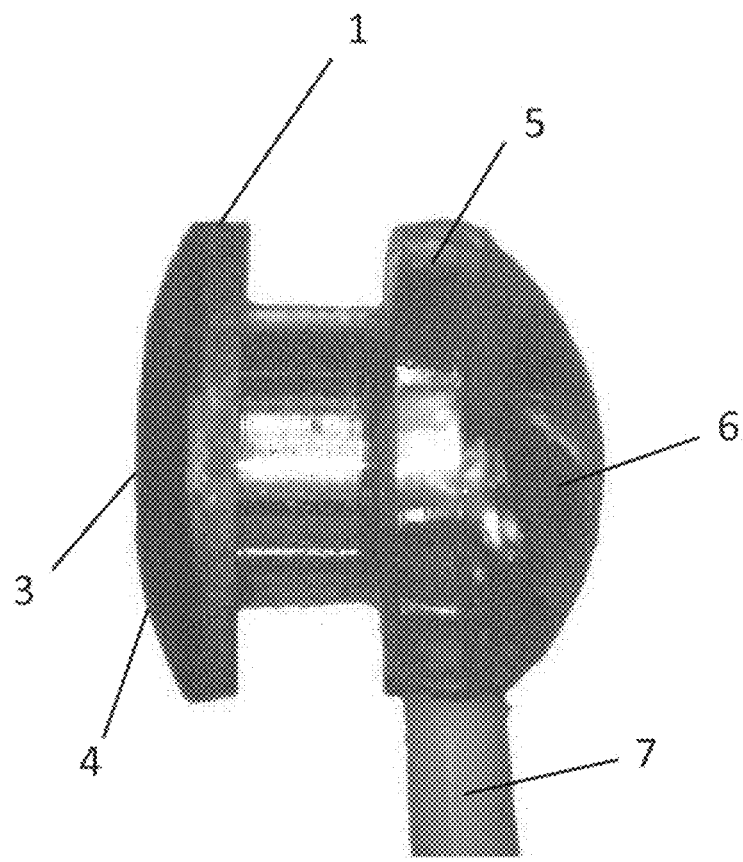
FIG. 2 is an image of an electrode according to the invention inserted in an electrode housing.

FIG. 2 is an image of the electrode 1 of FIG. 1 comprising a substrate 2, a skin contact part 4, a coating 3, and an electrode housing 5 comprising a sealing means 6 and connection means 7.

Figure 3:
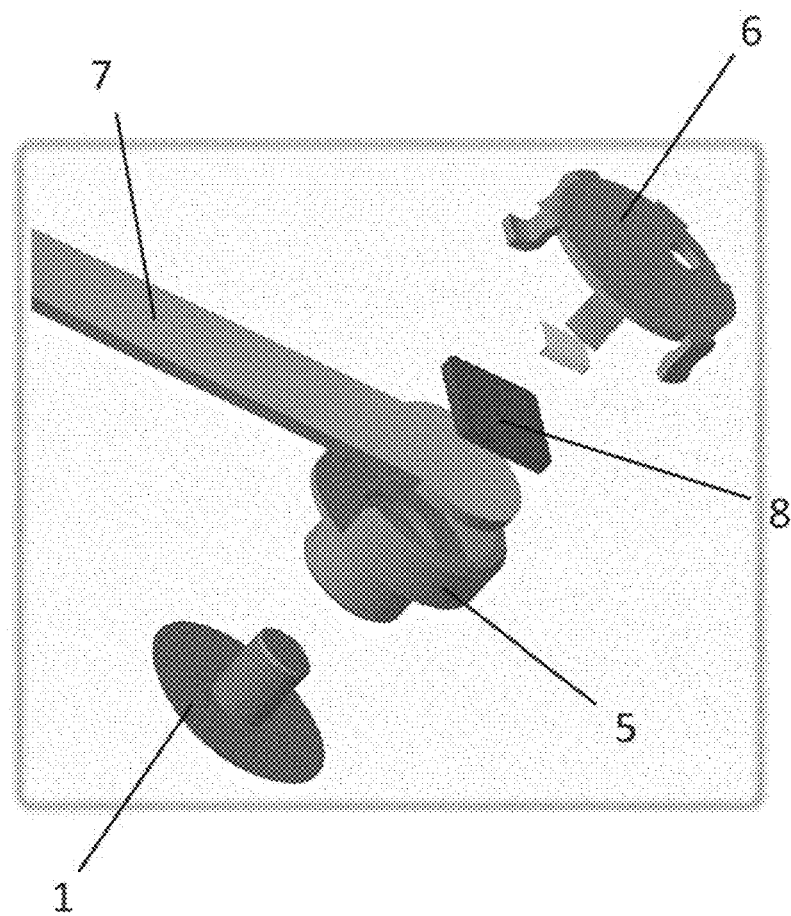
FIG. 3 is an exploded view of another embodiment of an electrode according to the invention.

FIG. 3 is an exploded view of another embodiment of an electrode according to the invention. In this embodiment, the connection means 7 is in the form of a flex PCB. Furthermore, a front-end ASIC 8 is shown.

Figure 4A:
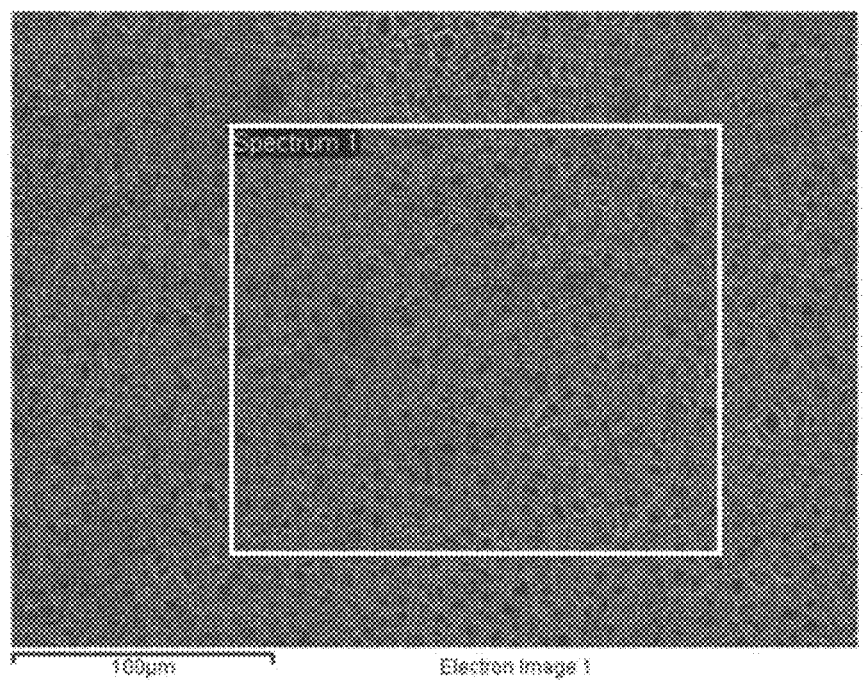
FIG. 4A and FIG. 4B are electron microscope images of the nanostructured surface pattern of the skin contact part of an electrode according to the invention.

FIG. 4A is an electron microscope image of the nanostructured surface pattern of the skin contact part of an electrode according to the invention. The image shows the nanostructured surface pattern comprising multiple ridges substantially evenly distributed over the skin contact part of the electrode which is covered by the coating. The multiple ridges form a grid of intersecting ridges. In this example, the width of a ridge is of a magnitude of approximately 1-10 µm.

Figure 4B:
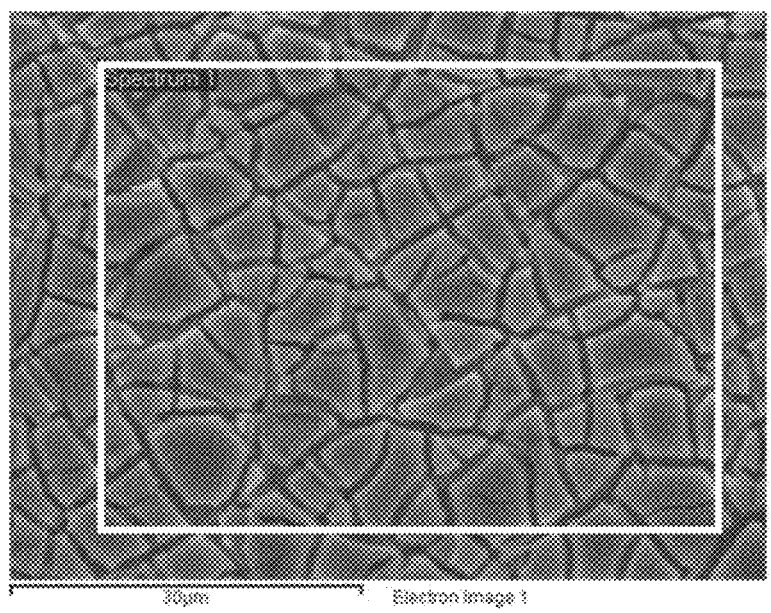

FIG. 4B is another electron microscope image of the nanostructured surface pattern of the skin contact part of an electrode according to the invention. As in FIG. 4A, the image shows the nanostructured surface pattern comprising multiple ridges substantially evenly distributed over the skin contact part of the electrode which is covered by the coating. The multiple ridges form a grid of intersecting ridges. In this example, the width of a ridge is of a magnitude of approximately 1-10 µm.

Figure 5:
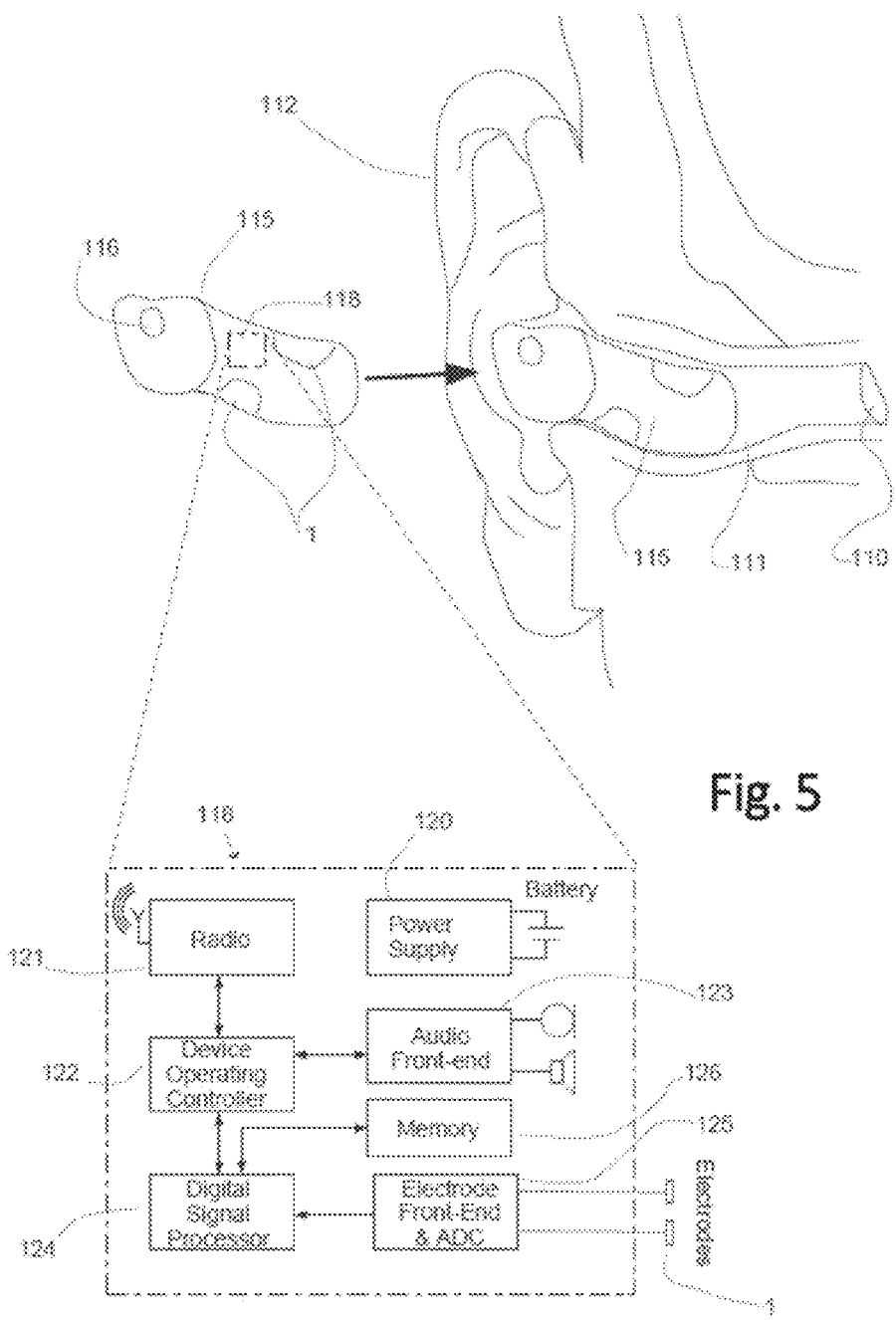
FIG. 5 is an ear device comprising electrodes according to the invention in a system view.

FIG. 5 shows an ear device comprising electrodes according to the invention in a system view.

The ear device 115 is adapted for monitoring EEG and can be worn inside the ear of a person to be monitored, e.g. for detecting Hypoglycemia, e.g. like a per se known In-The-Canal (ITC) hearing aid. Furthermore, the device will allow healthcare personal to remote monitor or record EEGs for several days at a time. Healthcare personal would then be allowed to monitor patients who have regularly recurring problems like seizures or micro-sleep. The ear device 115 will not interfere with normal life, because the ear device 115 has an acoustic vent 116 so the wearer will be able to hear. After a while, the wearer forgets that he wears the ear device 115. The ear device 115 is on its outer surface provided with two active electrodes 1 according to the invention. Internally the ear device 115 contains an electronic module 118.

The ear device 115 is formed to fit into the external auditory canal 111 of the wearer, and defines a cavity in the external auditory canal 111 together with the tympanic membrane 110, and the cavity is opened by means of the acoustic vent 116 extending through the entire length of the ear device 115. Preferably the ear device 115 does not extend beyond the pinna 112.

The electronic module 118 is shown schematically in enlarged view in the dotted box 118. The electronic module 118 includes a power supply 120 based upon a standard hearing aid battery for powering the electronics. The two electrodes 1 provided on the surface of the ear device 115 pick up a potential and delivers the data via a module 125 operating as electrode frontend and Analog to Digital Converter (ADC) to a digital signal processor 124. The digital signal processor 124 receives the amplified and digitized signal for processing. According to one embodiment, the digital signal processor 124 analyses the EEG signal picked up for detecting hypoglycemia by monitoring the brain wave frequency, and if the brain wave frequency falls beyond a predefined interval, this may indicate that a medical emergency may arise. Hypoglycemia is a medical emergency that involves an abnormally diminished content of glucose in the blood. Upon detection of abnormal brain wave activities, the digital signal processor 124 communicates these findings to a device operating controller 122.

The device operating controller 122 is responsible for several operations and has an audio front-end module 123 including a microphone and a speaker. With the microphone, the device operating controller 122 is able to pick up audio samples and classify the current sound environment. Furthermore, the device operating controller 122 may have access to real time clock information—either from an internal clock module or from a personal communication device (e.g. a smartphone) accessible via a radio module 121. The personal communication device and the radio module 121 may establish a wireless communication link by means of a short range communication standard, such as the Bluetooth™ Low Energy standard. The device operating controller 122 adjusts the predefined interval for normal the brain wave activity in dependence to the real time clock information and the sound environment classification. With the speaker, the device operating controller 122 is able to alert the wearer of the ear device 115 that medical emergency may arise and that precautionary actions have to be taken.

The number of electrodes has so far been identified as a pair of active electrodes operating in differential mode. However, two or more active electrodes may be acting as sensing electrodes for measuring the electric potential difference relative to an active electrode acting as a common reference electrode. The electrodes will operate in a unipolar lead mode.

The ear device 115 may in a further embodiment operate as a hearing aid if the processor is provided with a gain for alleviating a hearing loss of the wearer. The ear device 115 may advantageously be integrated into an In-The-Canal (ITC) hearing aid, a Receiver-In-Canal (RIC) hearing aid or another type of hearing aid.

An ear device according to the proposed invention may be used for continuous monitoring of EEG signals indicative of a medical seizure like hypoglycemia, epilepsy, or similar conditions. The device is used to foresee a seizure by analyzing the EEG signal by a digital signal processor and notify the user in case the analyzed signal indicates a potential seizure. The signal processor is continuously evaluating the EEG recording with statistical data analysis and machine learning methods.

The signal processor, power supply means, microphone, loudspeaker etc. may be located at the ear device or at a behind-the-ear (BTE) part. Whether these parts are located at the ear device or in the BTE part depends on the size and shape of the ear canal i.e. whether the ear insert is large enough for accommodating all components.

The size of the electrode plates is limited due to the physical size of the ear canal and hereby the surface of the ear device, consequently the capacitance of the electrode is limited, due to the small electrode capacitance. The impedance of the amplifier should be kept high. The frequency characteristic of the matching circuit should present a high pass filter having a cut off frequency of approximately 1 Hz.

The size of the electrodes is a tradeoff between being able to fit several electrodes within a confined space, and the capacitance of the electrode being proportional to the area, pointing to large electrode sizes. A preferable size is between 5 mm$^2$ and 100 mm$^2$. The electrode may be flexible but is preferably pre-shaped in a double curved shape to best fit the area of the ear, where it is to be placed. The monitoring device has several electrodes, where each one of them may have an individual shape, to best fit that particular area, where it is supposed to fit the user.

The ear device can be placed in the ear by the user, without help from trained personnel.

In one embodiment, the ear device can operate on batteries or other small independent power source, using approximately 1 mW.

The ear device records bioelectrical signals of the user, for example EEG. By use of advanced statistics and machine learning techniques, abnormalities or specific changes in patterns in the EEG can be characterized. This may be used for monitoring or determining neurologic disorders, or neurogenerative disease, and this can be used for e.g. warning a person or a relative about potentially epilepsy seizure, a hypoglycemic attack etc.

The ear device may further be used for improving the treatment of dementia, by tracking specific changes in the EEG. Other areas of use is diagnosis and rehabilitation of sleep, prevention, rehabilitation and treatment evaluation of psychiatric and emotional disorders, fatigue detection, brain-computer-interface.

The ear device may have many different shapes, the common goal for all shapes being, to have an ear insert that gives a close fit to the user's skin and is comfortable to wear, meaning that it should occlude the ear as little as possible.

In one embodiment the ear device comprises a customized shape for the ear canal of the user. The ear device is a hollow shell and made for the specific ear canal according to an imprint of the ear canal. The electrodes may be mounted on the inside or outside of the hollow shell. If mounted on the inside of the shell, the shell itself may be sufficient dielectric to ensure pure capacitive coupling, furthermore mounting the electrodes on the inside of a shell makes wiring of the electronic easier, than by outside mounting of the electrodes.

In another embodiment, the ear device comprises a pipe, where the electrodes may be mounted on the inner or outer circumference of the pipe. The pipe is made in different diameters, as to best fit the diameter of the ear canal. The pipe can also be shaped to fit the shape of the ear canal in the longitudinal direction. On the outer circumference the pipe is covered with a soft and flexible material like silicone, foam, rubber or other soft materials that ensures a secure and comfortable fit for the user.

In another embodiment, the ear device is in the form of a stent. Stents have the advantage, that they are flexible, can be inserted into the ear canal in a contracted state, where after it is released to form a close-fitting ear device.

In FIGS. 6A and 6B a soft-earpiece 10 for a left ear is shown. The soft-earpiece 10 comprises electrodes according to the invention inserted in positions A, B, C, T, E, and I, indicated by ELA, ELB, ELC, ELT, ELE and ELI in FIGS. 6A and 6B.

FIG. 6C is a representation of an earpiece 10, with indication of the means used to improve skin contact for dry-contact electrode recordings using electrodes according to the invention. The shortest dotted line 11 indicates the position of a flexible joint of the earpiece, while the longer and curved dotted line 12 indicates a cross-section of the rim of the ear-piece, where it can be seen that the rim of the ear-piece 10 is thicker than the rest of the ear-piece 10 to achieve a more rigid structure. It can also be seen that the electrode-holder is made so that the electrode will protrude from the surface of the ear-piece 10.

Figure 7A:
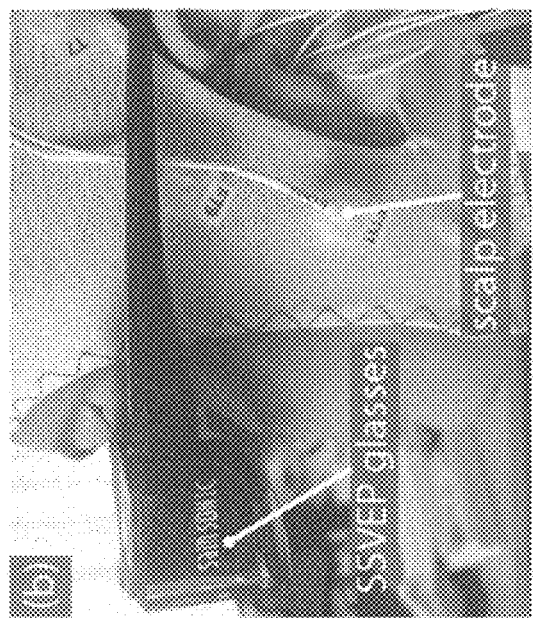
FIG. 7A is a picture of an earpiece with insert earphone mounted in an ear.

FIG. 7A is a picture of an earpiece with insert earphone mounted in an ear of a test subject in the comparative test described at the end of the description of this patent application.

Figure 7B:
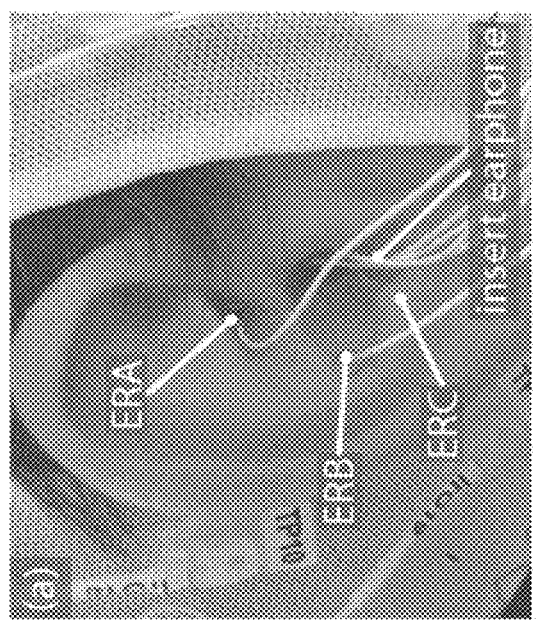
FIG. 7B is a picture of a test subject wearing SSVEP glasses and a cap with $IrO_2$ scalp electrodes.

FIG. 7B is a picture of a test subject wearing SSVEP glasses and a cap with $IrO_2$ scalp electrodes.

Figure 8A:
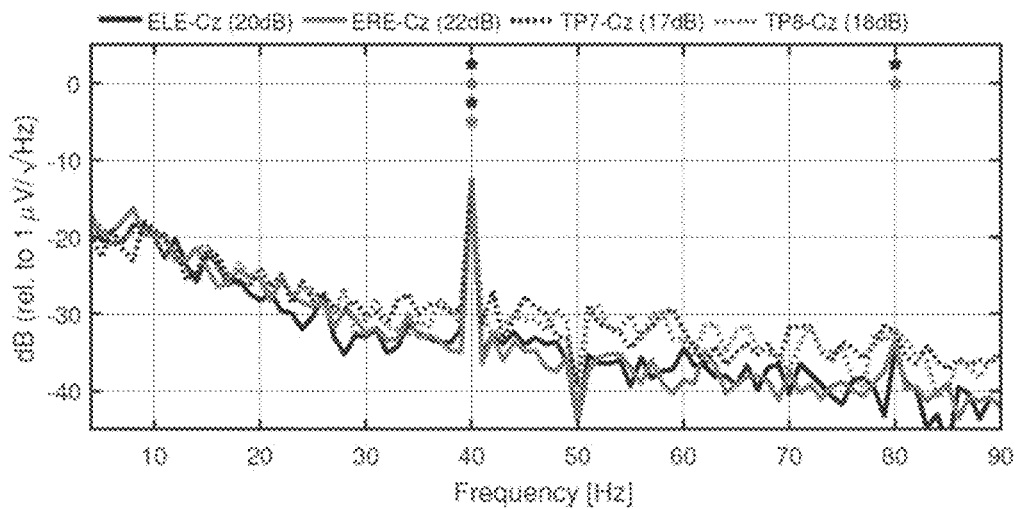
FIGS. 8A and 8B are graphs showing Grand average power spectra of ASSR for a Cz reference (FIG. 8A) and within-ear (FIG. 8B) reference configuration.
Figure 8B:
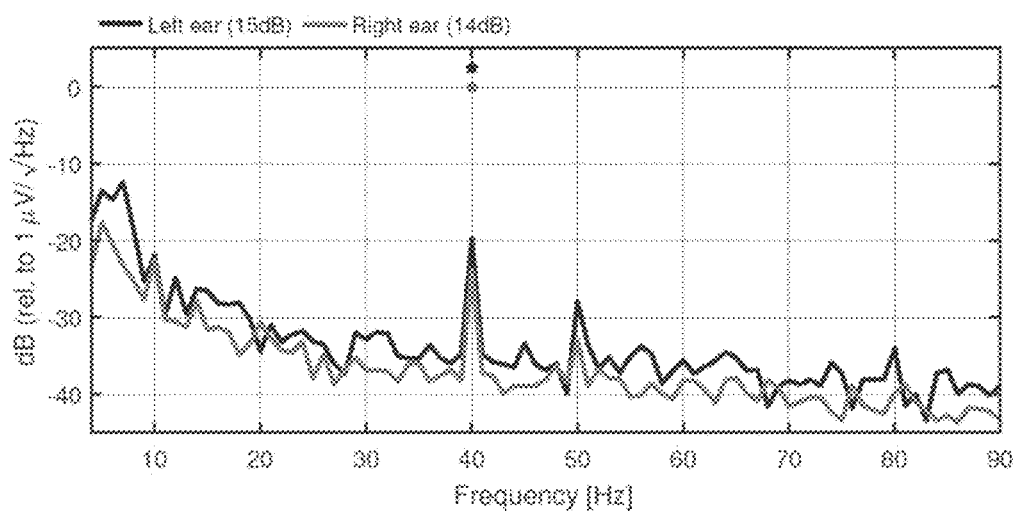

FIGS. 8A and 8B are graphs showing Grand average power spectra of ASSR for a Cz reference (FIG. 8A) and within-ear (FIG. 8B) reference configuration. The faded lines are the response for each subject. The SNR of the first harmonic response is given in the legends, and a star marker indicates a statistical significant, $p<0.05$, response, based on an F-test.

Figure 8C:
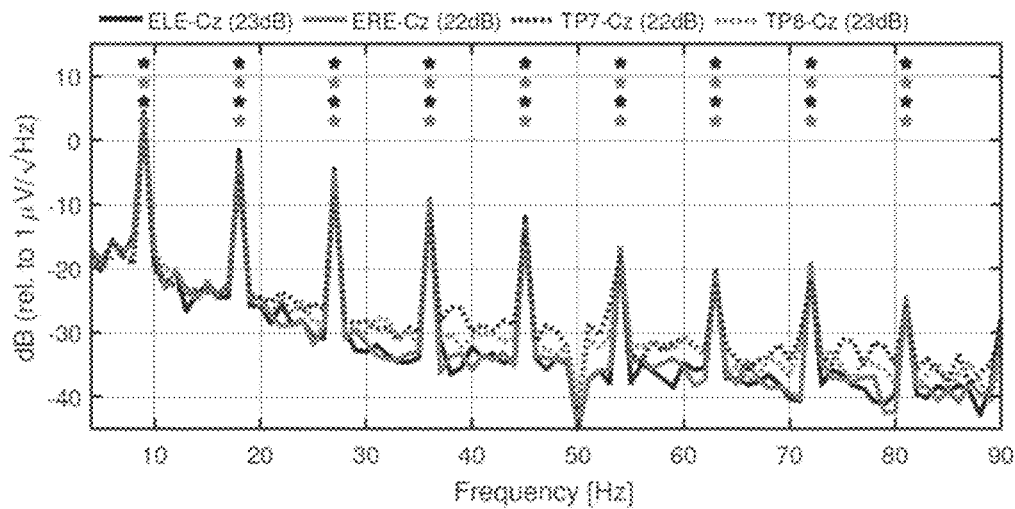
FIGS. 8C and 8D are graphs showing Grand average power spectra of SSVEP for a Cz reference (FIG. 8C) and within-ear (FIG. 8D) reference configuration.
Figure 8D:
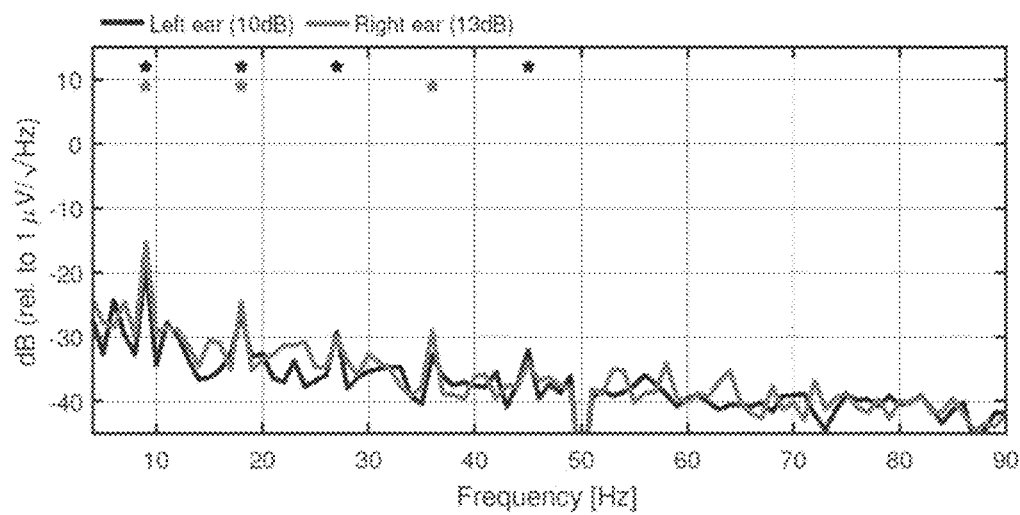

FIGS. 8C and 8D are graphs showing Grand average power spectra of SSVEP for a Cz reference (FIG. 8C) and within-ear (FIG. 8D) reference configuration. The faded lines are the response for each subject. The SNR of the first harmonic response is given in the legends, and a star marker indicates a statistical significant, $p<0.05$, response, based on an F-test.

Figure 9A:
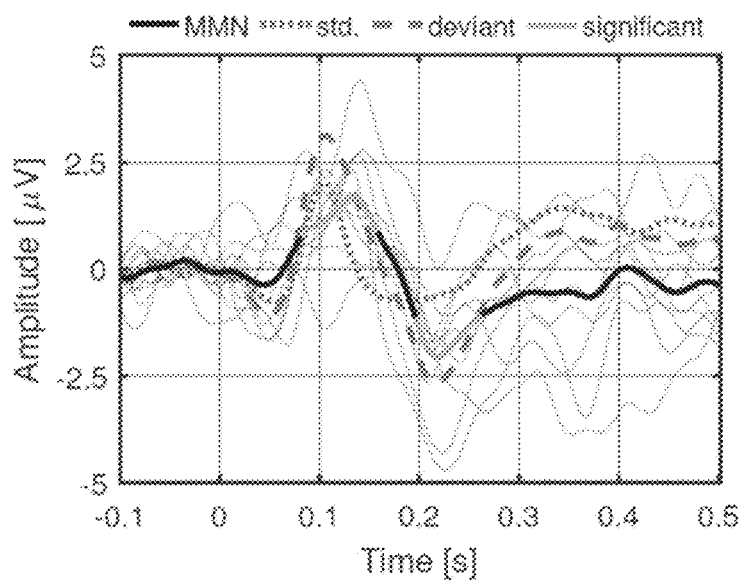
FIGS. 9A, 9B and 9C are graphs showing the Grand averaged MMN responses for different reference configurations.
Figure 9B:
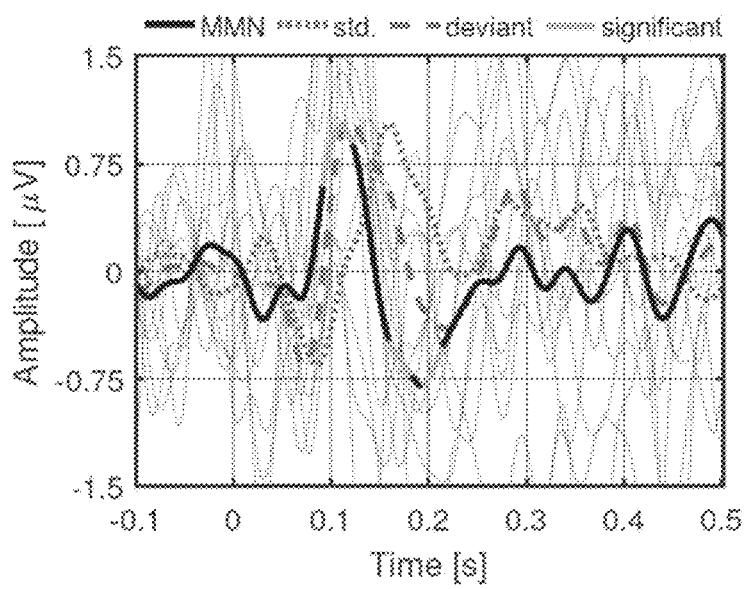
Figure 9C:
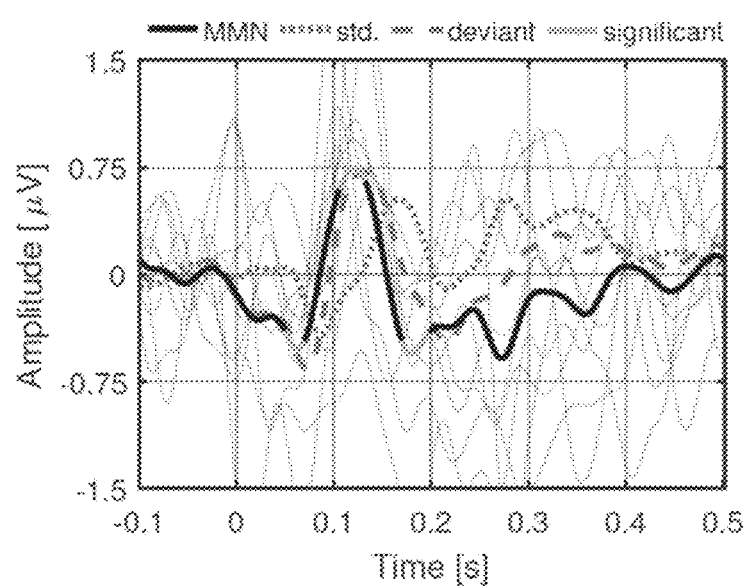

FIGS. 9A, 9B and 9C are graphs showing the Grand averaged MMN responses for different reference configurations. The faded lines are the MMN response for each subject. The dotted line show the response to standard stimuli, the dashed line shows the response to the deviant stimuli, and the solid line shows the difference between the deviant and the standard response (i.e. the MMN-response).

Figure 10A:
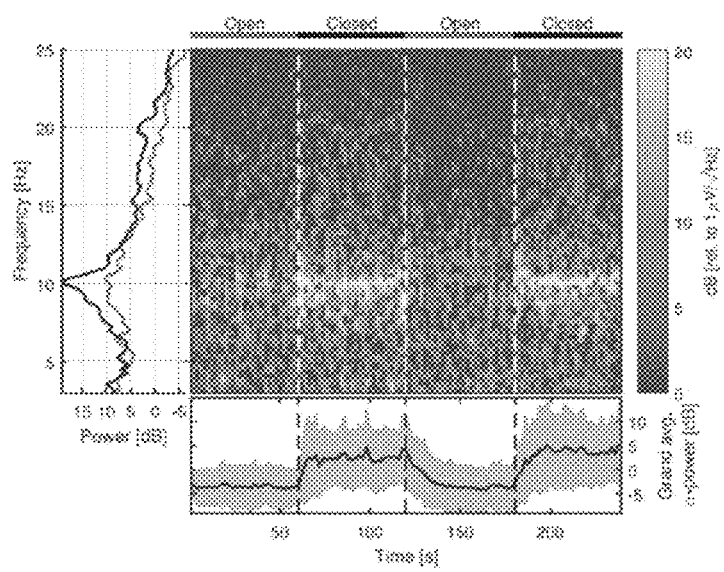
FIG. 10A is a graph showing a power spectrum and spectrogram for subject 11 of a study, included in the last section of this description, with indication of open and closed eyes intervals.

FIG. 10A is a graph showing a power spectrum and spectrogram for subject 11 of a study with indication of open and closed eyes intervals.

Figure 10B:
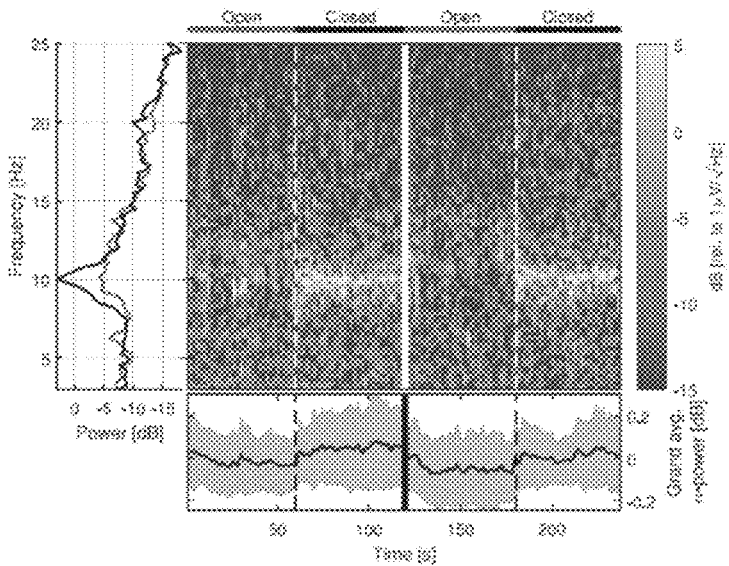
FIG. 10B is a graph showing Grand average of the mean alpha band power.

FIG. 10B is a graph showing Grand average of the mean alpha band power ([8; 12] Hz). The grand average plots have been smoothed with a 3 tap mean filter. All dB values are relative to 1 $\mu V/\sqrt{Hz}$.

Figure 11A:
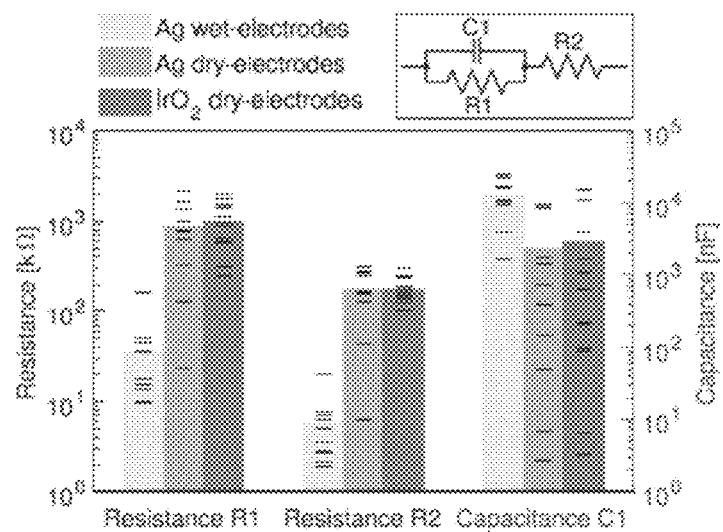
FIG. 11A is a graph showing a comparison of parameter values for a parametric model of the electrode-skin interface shown in the legend.

FIG. 11A is a graph showing a comparison of parameter values for a parametric model of the electrode-skin interface shown in the legend. The black lines indicate parameter values for single recordings.

Figure 11B:
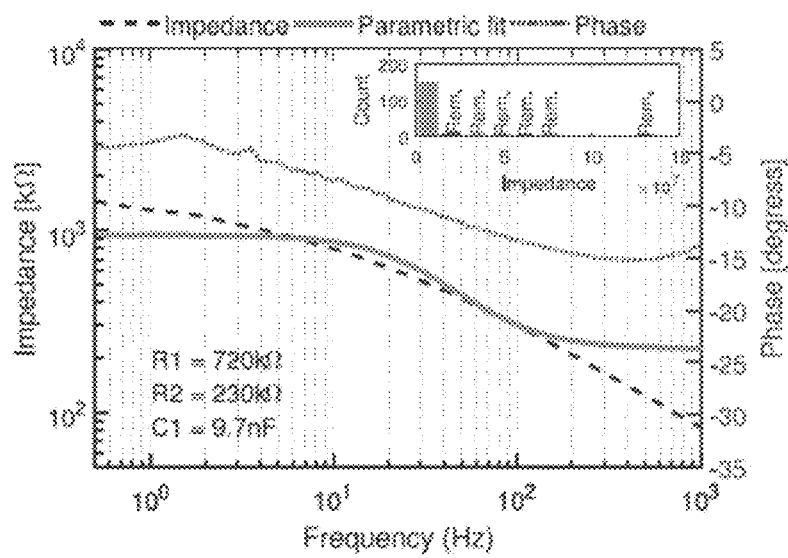
FIGS. 11B and 11C are graphs showing impedance spectra for dry-contact $IrO_2$ electrodes according to the invention.
Figure 11C:
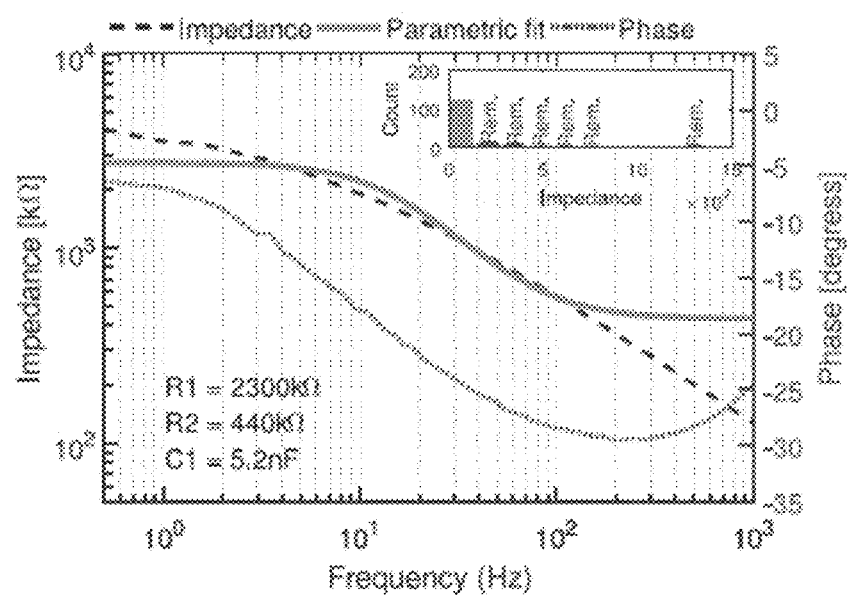

FIGS. 11B and 11C are graphs showing impedance spectra for dry-contact $IrO_2$ electrodes according to the invention. All impedance measurements were performed with earpieces inserted into the ears of the test subjects. FIG. 11B shows data for electrodes placed in the ear canal of a user, whereas FIG. 11C shows data for electrodes placed in the conchae. The histogram in the upper right corner of 11B and 11C, respectively, show the distribution of the mean impedance from 0.1 Hz to 10 Hz. A few recordings, marked by "Rem.", were outliers in the histogram and left out of the analysis of the study.

Comparative Test Results

Objective: Ear-EEG is a recording method where EEG signals are acquired from electrodes placed on an earpiece inserted into the ear. Thereby, ear-EEG provides a non-invasive and discreet way of recording EEG, and has the potential to be used for long-term brain monitoring in real-life environments. Whereas previously reported ear-EEG recordings have been performed with wet electrodes, the objective of this study was to develop and evaluate dry-contact electrode ear-EEG.

Methods: To achieve a well-functioning dry-contact interface, a new ear-EEG platform was developed. The platform comprised actively shielded and nanostructured electrodes embedded in an individualized soft-earpiece. The platform was evaluated in a study of 12 subjects and four EEG paradigms: auditory steady state response, steady-state visual evoked potential, mismatch negativity and alpha band modulation.

Results: The prototyped dry-contact ear-EEG platform was compared to conventional scalp EEG, for both scalp and ear reference configurations. The performance of the platform was on par with scalp EEG measured by electrodes close to the ear, when all electrodes were referenced to a common scalp electrode (Cz). With the reference electrode located within the ear, statistically significant (p<0.05) responses were measured for all paradigms, although for mismatch negativity it was necessary to use a between-ear reference configuration to obtain a statistical significant response.

Conclusion: The study demonstrated that dry-contact electrode ear-EEG is a feasible technology for EEG recording.

Significance: The prototyped dry-contact ear-EEG platform represents an important technological advancement of the method in terms of user-friendliness, because it eliminates the need for gel in the electrode-skin interface.

INTRODUCTION. For decades, researchers and clinicians have been eager to measure EEG outside controlled laboratory environments. In recent years, the interest for this have increased due to major developments within wearable devices, and a need for better and more efficient health care technologies. Ambulatory EEG systems exist and enable long-term real-life recordings, but they are typically bulky and obtrusive for the user's everyday life activities, and must be mounted by trained personnel [1]. Wearable EEG systems try to overcome the limitations of ambulatory systems, aiming at user friendly systems which are easy to mount and enable long-term recordings in the everyday life. Some wearable EEG systems take this trend even further and are designed to not attract attention during everyday life activities [2] [3] [4]. Conventional laboratory EEG recordings are performed with full cap systems and wet electrodes to obtain high quality measurements with high spatial resolution. Wearable EEG systems typically have lower spatial resolution and dry-contact electrode technologies are used to improve the user friendliness and quality of long-term recordings.

For dry-contact electrodes, no electrode gel is applied between the electrode and skin, instead the instrumentation and electrode is designed to accommodate and reduce the effect of variations in the electrode-skin interface [5] [6]. Dry-contact electrodes have been proposed in various designs, including mesh electrodes laminated onto the skin [3], flexible polymer based electrodes [2] [7] [8], and spring-loaded electrodes [9] [10].

Ear-EEG is a method where EEG is recorded from electrodes in the outer ear [11] [12]. Ear-EEG addresses the practical challenges of non-invasive and robust EEG acquisition in real-life environments. The shape of ear-EEG devices are very similar to the earpieces used for hearing aids and provides a discreet and comfortable way of recording EEG. Thus, wearable EEG systems based on ear-EEG could be used for monitoring of EEG for several days [4].

Previous ear-EEG recordings have been performed with wet electrodes, where conductive gel was applied between the electrodes and the skin [11] [13] [12]. Dry-contact electrode ear-EEG would increase the comfort and user-friendliness of ear-EEG devices, and enable the user to insert the device without assistance. In addition, the skin preparation, typically needed for wet ear-electrodes, could be avoided [5].

Here is presented a novel dry-contact ear-EEG platform, comprising dry-contact electrodes and a soft-earpiece. The electrode and earpiece design was validated through a study of standard EEG paradigms. Recordings performed with the dry-contact ear-EEG platform were compared to standard wet electrode scalp EEG recordings.

The study was approved by the regional scientific ethics committee (case no: 1-10-72-46-17).

II METHODS. This section is divided into four main parts. The first part (Sec. II-A and II-B) describes the novel dry-contact ear-EEG platform. The second part (Sec. II-C) describes the experimental setup. The third part (Sec. II-D, II-E, II-F, and II-G) describes the experimental paradigms and signal processing methods used to assess the quality of the recorded EEG signals. And finally, part four (Sec. II-H and II-I) describes evaluation methods for characterization of the electrode-skin impedance and half-cell potential.

A. Dry-contact ear-EEG electrodes. Recording of bioelectrical signals from electrodes placed on the surface of the skin relies critically on the electrode-skin interface. For dry-contact electrodes this interface is mainly defined by the electrochemical properties of the electrode material, the mechanical design of the electrode, the surface properties of the electrode, and how the electrode is retained against the skin. Thus, a good dry-contact electrode interface for ear-EEG relies both on the electrode itself and how it is mounted in the ear. This subsection describes the developed electrode, and the following subsection describes the soft earpieces used for the electrode.

The electrode was based on a titanium (Ti) pin coated with iridium-oxide ($IrO_2$) and mechanically designed to be embedded into a soft-earpiece. $IrO_2$ is a well characterized material with pseudocapacitive properties and low impedance. $IrO_2$ coatings have previously been used for both tissue stimulation [14] [15] and measurements of biopotentials [16].

The $IrO_2$ coating for the current study was a thermal iridium oxide film (TIROF) formed on an etched Ti surface [17] [18]. The electrode was evaluated biocompatible by UL (2017, Germany), according to the EN ISO 10993-1 standards. The coating is mechanical robust and highly inert, thus suitable for long term skin contact during recordings in the everyday life. In addition, the coating has hydrophilic properties, causing it to easily become moistened, when applied to the skin.

The electrode assembly was based on a circular $IrO_2$ coated Ti-pin electrically shielded by a housing made of silver (Ag). The Ti-pin and the shielding house was electrically isolated by a spacer made of polymer, as shown in FIGS. 1 and 2. The core of a coax cable was connected to the Ti-pin, and the shield of the cable was connected to the housing. Epoxy adhesive was applied to strengthen the construction.

The electrode was designed to be inserted in holes in a soft earpiece, as shown in FIG. 6A. Previous ear-EEG earpieces have been constructed of rigid acrylic plastic with electrodes made of silver epoxy painted onto the surface of the earpiece. Thus, the electrodes could not be reused for another earpiece. The designed $IrO_2$ electrode is generic and can be moved from one earpiece to another.

B. Soft-earpieces. To obtain a firm electrode-skin contact, we found it to be of crucial importance to have the developed electrode mounted in a soft-earpiece customized to the anatomical shape of the individual ear. This was particularly important to achieve good and reliable contact in the concha part of the ear. The flexibility of the earpiece allowed it to follow changes in the shape of the ear, and helped the electrodes to maintain a stable contact with the skin during these changes. For the current study, electrode holes were created in positions ExA, ExB and ExC in the concha part of the outer ear, and positions ExE, ExI and ExT in the ear-canal, where x denote the left (L) or right (R) ear [11]. The ExT electrode was facing the tragus of the ear. FIGS. 6A and 6B show the position of the electrodes on an earpiece.

Earpieces for the study were designed with a flexible joint between the ear-canal and concha part of the earpiece, as shown in FIG. 6C. This enabled the ear-canal and concha part of the earpiece to move independently, facilitating less motion of the electrodes during e.g. jaw movements [19]. The ExT electrode and the electrodes located in concha were mounted in flexible bearings elevated towards the skin, creating an increased skin pressure at the location of the electrode. The electrodes located in the concha are especially prone to lose skin contact. Therefore, the concha electrodes were located at the rim of the earpiece, where the C-shape between concha cymba and anti tragus helped to create pressure towards the skin. The earpieces were made of biocompatible elastic earmould silicone (Detax Softwear 2.0, Shore A 60).

C. Experimental setup. The dry-contact ear-EEG platform was tested in an EEG study of 12 subjects. The EEG recordings were acquired with a sampling rate of 500 Hz by a 32 channel portable TMSi MOBITA EEG amplifier (TMSi, The Netherlands). The amplifier was characterized by a high input impedance (>4 GΩ), low noise (<0.4 µV@0.1 to 10 Hz), and guarded wires, which enabled active shielding of the ear-electrodes all the way to the backside of each of the 12 electrodes. An easycap (Easycap, Germany) containing 20 wet $IrO_2$ electrodes were used for scalp recordings, as shown in FIG. 7B. The scalp electrodes were positioned according to the 10-20 system. A conductive bracelet on the right arm was connected to the GND of the EEG amplifier. Prior to insertion of the earpieces, the ears were cleaned with alcohol and water.

12 subjects (1 female) with normal hearing and vision aged on average 30.9 (std=5.6) years, participated in the study. The recordings were performed in a laboratory, where the subject was seated in the comfortable chair and instructed to relax.

The stimulus for the steady-state visual evoked potential (SSVEP) was given by modified active shutter glasses (SSVEP glasses), as shown in FIG. 7B. The electronics in the glasses were removed and wires were connected directly to the LCD panel, covering the lenses of the glasses. Thereby it was possible to modulate the ambient light. The modulation was controlled by a 5 V 50% duty cycle signal. The rise and fall time of the modulation were 20 µs and 1000 µs, respectively.

For the auditory paradigms, the audio was presented to the subject by insert earphones (3M E-A-RTONE™ GOLD) with equal phase and intensity in both ears. The tubes from the earphones were inserted into the vents of the earpieces. The stimuli were presented at a sound level of 55 dB above the individual hearing threshold, measured at 1000 Hz. During the auditory paradigms, the subject was watching a silent movie without subtitles.

All recordings were bandpass filtered with the EEGLAB FIR filter function "pop eegfiltnew( )" [20]. The cutoff frequencies of the filter are given below for each paradigm.

D. Discarding of ear-electrodes. To locate electrodes with a bad skin contact, a 40 Hz auditory steady-state response (ASSR) was used as a basis for electrode discarding. For each ear-electrode, all possible reference configurations within the same ear was explored. Electrodes where none of the reference configurations resulted in a statistical significant ASSR (F-test, $p<0.05$) was discarded from the data analysis.

More specifically, the data were bandpass filtered from 2 to 100 Hz and segmented in 1 s segments. For each reference configuration the 256 segments with the lowest mean power from 55 to 75 Hz were selected. The ASSR was extracted by time-domain averaging (TDA) of the segments, and the SNR was calculated as the ratio between the power of the first harmonic ASSR (at 40 Hz), and the mean power from 45 to 55 Hz (40 Hz excluded).

E. Steady-state responses. Two steady-state stimuli were studied. Each of the stimuli was presented to the subject for 5 minutes.

The ASSR stimulus was Gaussian distributed white noise amplitude modulated with 40 Hz. The SSVEP stimulation was performed by modulating the ambient light with 9 Hz by using the SSVEP glasses presented above. The subject was seated in front of a 40" monitor displaying a white screen. The distance from the forehead to the monitor was 600 mm.

The recordings were bandpass filtered to retain frequencies between 2 and 100 Hz, and a second order 50 Hz notch-filter was applied to reduce power line interference. Then, the data were segmented in 1 s segments. To ensure coherent averaging of the steady-state responses (SSRs), the segments were aligned to 8 Hz triggers for the ASSR and 9 Hz triggers for the SSVEP. For Cz referenced data, the 256 segments with the lowest mean power from 55 to 75 Hz were selected, and TDA of the segments were performed.

When ear-electrodes are referenced to electrodes within the same ear, the power of the SSR naturally decrease, because of small electrode distances, compared to scalp referenced ear-electrodes [11] [19]. The lower amplitudes imply that the reference configuration must be optimized for each subject to obtain a reliable response [21]. Thus, to obtain a reliable SSR for all subjects, the reference configuration was carefully selected for each subject. To avoid over-fitting, the reference configuration was trained on half of the extracted segments, and tested of the other half of the segments. This cross-validation was performed a 100 times, and the TDA of all test data was calculated.

Specifically, for each cross-validation, the training was performed with 128 segments randomly selected from the 256 segments with the lowest mean power from 55 to 75 Hz. Then, the reference configuration causing the highest SNR of the first harmonic SSR was selected. Testing was performed with the selected reference configuration and the remaining 128 segments. The SSR was calculated as the TDA of the test data for 100 cross-validations.

For SNR calculations, the signal was the power of a harmonic of the SSR, and the noise was the mean power of +/−5 Hz relative to the signal frequency. The signal frequency was excluded from the noise estimate. The SNR was calculated as the ratio between the signal and noise.

F. Mismatch negativity. The standard stimuli were a 1 kHz sinusoid of duration 75 ms (including 5 ms rise and fall times). The deviant stimuli were deviating in frequency (2 kHz) and randomly selected with a probability of 0.2. The stimulus-onset asynchrony (SOA) was randomly chosen between 500 and 800 ms. A total of 2000 stimuli (400 deviants) were presented in two 11 minutes sequences.

The recorded EEG data were bandpass filtered from 1 to 25 Hz and segmented with limits of −100 to 500 ms relative to the onset of the stimulus. The noise level for each epoch was estimated as the mean power from 55 to 75 Hz, based on the unfiltered EEG data. The event related potential (ERP) to the standard stimuli was extracted by TDA of 512 segments, the 256 segments with the lowest noise level were selected from each sequence. Similarly, the ERP to the deviant stimuli was extracted by TDA of 256 segments, where the 128 segments with the lowest noise level were selected from each sequence. The mean amplitude from −100 to 0 ms was used for baseline correction.

G. Alpha band modulation. To complement the steady-state and event-related responses, the study also comprised recordings of spontaneous EEG. The study focused on alpha band activity, which is modulated by visual attention.

The subject was instructed for two conditions; 1) Eyes open, watching the silent movie. 2) Relaxing with closed eyes. An auditory cue indicated a change in condition every 60 second. The first condition was always condition 1. The measurement had a duration of 4 minutes.

The EEG data were bandpass filtered from 2 to 45 Hz and segmented in 4 s segments, overlapping 2 s. For each segment the mean alpha power, [8, 12] Hz, was calculated. Segments with a mean alpha power above 100 $\mu V^2/Hz$ for a Cz reference and 1 $\mu V^2/Hz$ for a within-ear reference were left out of the analysis.

The primary alpha sources during closed eyes are occipital, and thus not within close proximity of the ear [22]. Considering the small electrode distances within the ear, it was necessary to optimize the within-ear reference configuration for each subject. The data were divided in two sequences, with the first sequence containing the first 120 s of data and the remaining 120 s in the other sequence. Then, the within ear reference configuration, causing the highest alpha band modulation ratio was located for each sequence. To avoid overfitting, the reference configuration causing the highest alpha modulation for each sequence was used for the analysis of the opposite sequence.

H. Electrode-skin impedance. To obtain a better understanding of the electrode-skin interface for the developed dry-contact ear-EEG platform, characterization of the electrode-skin impedance spectrum was performed for all subjects. Impedance spectra were measured for all 12 ear-electrodes in the end of the study, where the subject had been wearing the earpieces for approximately 2 hours.

The electrode-skin impedance for wet and dry-contact ear-EEG electrodes have previously been characterized for silver (Ag) electrodes in [5]. The study described equipment to measure the impedance spectrum, and presented impedance spectra for the electrodes. The same equipment was used to characterize the electrode-skin impedance for the developed $IrO_2$ dry-contact electrode.

The impedance measurements were performed with a current density of 0.5 $mA/cm^2$, and impedance spectra were measured between 10 combinations of the 6 electrodes in each ear. This enabled a robust estimation of the electrode-skin impedance for a single electrode (single electrode-skin interface). 6 of the impedance measurements, for each ear, were performed between an ear-electrode and a conductive bracelet on the left arm. The GND of the impedance setup was always connected to a conductive bracelet on the right arm. The impedance spectra and parameters for an electrical model of the electrode-skin interface were estimated as described in [5].

I. Half-cell potential. The half-cell potential was measured for 5 electrodes where only the $IrO_2$ coating was exposed. All measurements were performed relative to a SI analytics 2820+ (2Ag/AgCl electrode in a 3 Mol KCl solution, ceramic membrane reference electrode. The electrodes were submerged in a container with 1 Mol KCl at temperature 25° C. The measured potentials were subtracted 27.7 mV, according to Nernst equation, to correct for the different KCl solutions in the container and reference electrode. The measurements were performed with a Rohde & Schwartz HMC 8012 multimeter (input impedance>10 $G\Omega$). For each measurement, the electrode was submerged in the container, 20 minutes later the half-cell potential was measured, and the electrode was removed and cleaned with water. This procedure was repeated 4 times for each electrode.

III. RESULTS. In the following we present EEG recordings performed with the developed dry-contact ear-EEG platform and wet scalp electrodes. The results are presented for different reference configurations, to illustrate how the response changed with the reference configuration.

According to the discard criteria given above, a few ear electrodes were discarded as given in Table I.

TABLE I

DISCARD RATIOS FOR THE DATA ANALYSIS, GIVEN FOR EACH EAR-ELECTRODE LOCATION. CONCHA ELECTRODES MARKED WITH GRAY.

| Left ear | | | | | | Right ear | | | | | |
| --- | --- | --- | --- | --- | --- | --- | --- | --- | --- | --- | --- |
| ELA | ELB | ELC | ELE | ELI | ELT | ERA | ERB | ERC | ERE | ERI | ERT |
| 0.3 | 0.2 | 0.3 | 0.2 | 0.3 | 0.1 | 0.0 | 0.2 | 0.3 | 0.1 | 0.0 | 0.1 |

A. Steady-state responses. FIGS. 8A and 8B show grand average ASSRs, and FIGS. 8C and 8D grand average SSVEPs. Power spectra for a Cz reference are shown in FIG. 8A and FIG. C, respectively, and FIGS. 8B and 8D, respectively, are for a within-ear reference, where the reference configuration was optimized for each subject, as described above. The SNRs of the first harmonic responses are given in the legends, and star markers indicate statistical significant responses (F-test, p<0.05). The ASSRs and SSVEPs were similar for scalp and ear-electrodes, for a Cz reference configuration. Looking at the within-ear referenced data, the SNR values were lower, but the first harmonic responses were still easily observable and statistical significant. The noise floor of the power spectra, was comparable for the within-ear and Cz reference configurations.

B. Mismatch negativity. Grand average MMN responses are shown in FIG. 9A for an ELE-Cz reference configuration, and FIGS. 9B and 9C for the between-ear configurations TP7-TP8 and ELE-ERE. The green line color indicates intervals where the MMN response was statistical significantly (p<0.05) different from zero, measured by a one sample t-test. The onset response for both the standard and deviant ERPs show the well-known P1-N1-P2 waveform, with timing and amplitudes similar to previous wet electrode ear-EEG recordings [13]. The timing of the responses changed slightly when the reference configuration was changed from Cz to between-ear. The MMN response is only shown for between-ear reference configurations as it was not statistical significant for within-ear configurations.

C. Alpha band modulation. FIG. 6 shows spectrograms with corresponding power spectra for recordings from a single subject. The plot below each spectrogram shows the grand average of the mean alpha power, [8, 12]Hz. For the calculation of the grand average mean alpha power shown in the figure, 8% of the Cz referenced and 9% of the within-ear referenced data were discarded, according to the criteria described above.

The spectrogram and grand average alpha power for the ELT-Cz configuration show a clear and statistical significant (p<0.001) alpha band modulation. For the within-ear reference configuration, the modulation was lower but the grand average modulation was still statistical significant (p<0.001). According to Table II the alpha modulation was statistical significant (p<0.05) for 9 out of 10 subjects for the ELE-Cz configuration, and 5 out of 12 subjects for the within-ear reference configuration.

TABLE II

| Subject | ELE-Cz | | Within-ear | |
| --- | --- | --- | --- | --- |
| | α mod. | p | α mod. | p |
| 1 | 3.6 | <0.001 | 1.1 | 0.016 |
| 2 | — | — | 1.1 | 0.412 |
| 3 | 2.1 | <0.001 | 1.2 | 0.060 |
| 4 | 1.1 | 0.705 | 1.8 | 0.220 |
| 5 | 3.1 | <0.001 | 0.9 | 0.160 |
| 6 | 2.4 | <0.001 | 1.5 | <0.001 |
| 7 | 1.5 | <0.001 | 0.8 | 0.126 |
| 8 | 6.6 | <0.001 | 1.4 | 0.021 |
| 9 | 2.6 | <0.001 | 1.9 | <0.001 |
| 10 | 1.9 | <0.001 | 1.1 | 0.296 |
| 11 | 3.7 | <0.001 | 2.4 | <0.001 |
| 12 | — | — | 1.1 | 0.725 |
| Grand avg. | 2.7 | <0.001 | 1.2 | <0.001 |

Alpha band modulation ratio for open/closed eyes, and corresponding P-values for an unpaired T-test. "—" Indicate discarded recordings.

D. Electrode-skin impedance. FIG. 7(a) shows grand averaged model parameters for wet and dry-contact silver (Ag) electrodes on rigid earpieces and grand averaged model parameters for the developed $IrO_2$ dry-contact electrodes. The parameters for the Ag electrodes are taken from [5]. The resistance and capacitance were comparable for the dry Ag and dry $IrO_2$ electrodes. For the dry-contact electrodes, R1 was dominating the resistive part of the electrode-skin interface. For comparison the impedance at approximately 50 Hz for ear-canal electrodes were 4 kΩ (std=3 kΩ) for wet Ag, 452 kΩ (std=737 kΩ) for dry Ag, and 435 kΩ (std=515 kΩ) for dry $IrO_2$.

FIGS. 7(b) and 7(c) show grand average impedance spectra for the dry $IrO_2$ electrodes in the ear-canal and concha, respectively.

The histogram in the upper right corner of FIGS. 7(b) and 7(c) display the distribution of the mean impedance from 0.1 Hz to 10 Hz. A few measurements, marked by "Rem.", were outliers in the histogram and left out of the analysis. In total, measurements from 12 (7.1%) electrodes were left out of the analysis.

E. Half-cell potential. The half-cell potential was measured to an average of 99 mV (std=29 mV), corresponding to a half-cell potential of 322 mV when referenced to the standard hydrogen electrode.

Measurements of the half-cell potential were performed in an electrolyte solution (1M KCl), and did not resemble dry skin contact. To supplement the half-cell potential measurements and obtain an estimate of the offset tolerance required to measure with the developed electrode on skin, the DC offset was calculated for all included ASSR recordings. The calculations were performed for ear-electrodes in both ears, and with average reference. The standard deviation of the offset for 122 measurements was 46 mV (min=−108 mV, max=176 mV).

IV. DISCUSSION. A. Steady-state responses. The first harmonic ASSRs were statistical significant for both scalp (Cz) and within-ear reference configurations. The amplitude of the first harmonic of the ASSRs decreased approximately 10 dB, when the reference was changed from the scalp to within-ear configuration. This decrease is smaller but still comparable to previous ear-EEG recordings based on wet electrodes [11] [13], and is primarily caused by the smaller electrode distances. However, the SNR of the ASSR decreased with 5-8 dB from the scalp to within-ear reference configuration. This is not consistent with previously reported results, where the SNR was similar or higher for within-ear referenced recordings [11] [19] [23]. The decreased SNR was caused by a similar noise floor of the power spectra for the scalp and within-ear reference configurations. This was most likely related to increased noise in the electrode-skin interface for dry-contact electrodes compared to wet electrodes.

The first 8 harmonics of the SSVEP were statistical significant for both scalp- and ear-electrodes when referenced to Cz. However, for the within-ear reference configuration it was only the first two harmonics which were consistently statistical significant. The amplitude of the SSVEPs were approximately 20 dB lower for within-ear referenced ear-electrodes compared to Cz referenced ear-electrodes. This is largely consistent with previously reported results for wet electrodes [11]. The SNR of the SSVEP decreased 9-13 dB from the scalp to within-ear reference configuration. As for the ASSR results, this was mainly due to a decreased SSVEP, while the noise floor of the power spectra for the scalp and within-ear reference configurations were similar.

B. Mismatch negativity. The MMN response for the ELE-Cz configuration had timing of the peaks which correspond to previous studies of MMN, where the reference configuration and paradigm was similar [24]. The first peak of the MMN response was elicited around 150 ms for a Cz reference, which is consistent with [25].

When the reference configuration was changed to TP7-TP8 and ELE-ERE, the amplitude of the MMN response was lower and the timing of the peaks were slightly changed. This is likely a consequence of the changed reference configuration, which results in a different weighting of the neural sources related to the MMN response.

The current study is the first to present a MMN response measured with ear-EEG, though it was necessary to utilize a between-ear reference configuration to obtain a statistical significant response.

C. Alpha band modulation. FIG. 6(a) shows a clear grand average alpha band modulation for the ELE-Cz reference configuration. When the reference was changed to within-ear, the grand average alpha modulation was less visible, but still statistical significant. Compared to previous studies of alpha band modulation performed with wet ear-electrodes, the modulation for the within-ear reference configuration was lower for the current study [19]. The lower modulation was probably related to an increased noise level for dry-contact electrodes, which was also observed for the SSR recordings. However, FIG. 6 clearly shows that alpha band modulation can be measured with the developed dry-contact ear-EEG platform.

D. Electrode-skin impedance. The model parameters for dry Ag and dry $IrO_2$ electrodes were comparable, even though the electrode area of the $IrO_2$ electrodes were approximately 1.5 times smaller than the area of the dry Ag electrodes. In addition, the Ag electrodes were painted on the surface of individualized rigid earpieces, causing the electrodes to follow the contour of the ear canal. The developed $IrO_2$ electrode has a fixed shape, which might cause the skin contact area to be smaller than the electrode surface area. Thus, the ratio between the contact area of the Ag and $IrO_2$ electrodes might be larger than 1.5.

The double-layer of the electrode-skin interface was modeled by C1 and R1, and R2 modeled the ohmic resistance of the electrolyte, skin and bulk tissue [6]. For dry-contact electrodes, the formation of a double layer is limited by the amount of moisture from the body condensed on the surface of the electrode. This cause the impedance of the double-layer to increase, compared to wet-electrodes. This could explain why R1 is dominating the resistive part of the electrode-skin interface for dry-contact electrodes.

In [5] impedance measurements for dry Ag electrodes located in the concha region of the ear were not included, due to extreme impedances for these electrodes. The current study illustrates that with soft-earpieces and $IrO_2$ electrodes, it is possible to obtain an acceptable electrode-skin impedance for dry-contact electrodes in the concha. However, the impedance for concha electrodes were higher than the impedance for ear-canal electrodes. This confirm practical experience of a more sensitive electrode-skin interface for electrodes in the concha region of the ear. In a previous study of physiological artifacts in ear-EEG [19], we speculated that soft-earpieces could be an improvement over rigid earpieces. The impedance measurements for concha electrodes confirm this speculation.

To measure EEG with the developed dry-contact electrode, the instrumentation must be designed appropriately. The primary focus should be on high input impedance and low input referred noise. The input impedance must be high to obtain sufficient common mode rejection ratio (CMRR), with high impedance mismatch between electrodes. The impedance mismatch is expected to be in the same order of magnitude as the electrode-skin impedance [5]. The CMRR of the system is limited by $CMRRelec \approx 20 \log 10\, Z_C/\Delta Z_E$, where $\Delta Z_E$ is the impedance mismatch and $Z_C$ is the common mode input impedance of the instrumentation amplifier [6] [5]. Regarding the input referred noise, the main focus should be on the current noise, because the current noise is multiplied by the electrode impedance; $n_{input}=v_n+Z_E \cdot i_n$, where $n_{input}$ is the total input referred noise, $v_n$ the input referred voltage noise, and $i_n$ the input referred current noise.

E. Half-cell potential. The measurements of the half-cell potential had a standard deviation of 29 mV, confirming a similar half-cell potential between electrodes and measurements. In addition, calculations of the required offset tolerance showed that an amplifier with an offset tolerance of at least 92 mV (2·std) is necessary to obtain reliable recordings with the dry-contact ear-EEG platform.

V. CONCLUSION. A novel dry-contact ear-EEG platform, comprising actively shielded and nano-structured electrodes embedded in individualized soft-earpieces, was developed and prototyped. The dry-contact ear-EEG platform was evaluated in a study of 12 subjects and four EEG paradigms: auditory steady-state response (ASSR), steady-state visual evoked potential (SSVEP), mismatch negativity (MMN), and alpha band modulation. For scalp referenced ear-electrodes, the ASSR and SSVEP were on par with measurements from scalp electrodes located near the ear. For within-ear referenced ear-electrodes, the ASSR and SSVEP were lower, which is consistent with previous studies and is due to the smaller electrode distances that can be achieved in the ear. Unfortunately, the noise floor of the recordings did not decrease as much as the steady-state responses, and in consequence a lower signal-to-noise ratio (SNR) was achieved. Despite of the lower SNR, the responses were clearly observable and statistical significant (p<0.05). For scalp referenced ear-electrodes the MMN waveform and timing corresponded well with literature. The MMN response was not observable for a within-ear reference, but for a between-ear reference configuration, the MMN response was observable and statistical significant. Alpha modulation related to open/closed eyes was clear and statistical significant for scalp referenced ear-electrodes. For a within-ear reference, the modulation was lower but still statistical significant. To gain insight into the electrode-skin interface for the developed dry-contact ear-EEG platform, the electrode-skin impedance spectra were measured and characterized for all subjects. The analysis of the impedance spectra confirmed practical experience of a more sensitive electrode-skin interface for electrodes in the concha region of the ear, compared to electrodes in the ear-canal. In addition, the measurements showed that the electrical instrumentation must be carefully designed to accommodate the high impedance of the dry-contact electrodes. Based on the study of both EEG and impedance spectra it is concluded that dry-contact electrode ear-EEG is a feasible technology for EEG recordings. We believe that the prototyped dry-contact ear-EEG platform represents an important technological advancement of the method in terms of user-friendliness, because it eliminates the need for gel in the electrode-skin interface.

REFERENCES

[1] A. J. Casson et al., "Wearable electroencephalography," IEEE Eng Med Biol Mag, vol. 29, no. 3, pp. 44-56, May/June 2010.

[2] J. H. Lee et al., "CNT/PDMS-based canal-typed ear electrodes for inconspicuous EEG recording," J Neural Eng, vol. 11, no. 4, p. 046014, June 2014.

[3] J. J. S. Norton et al., "Soft, curved electrode systems capable of integration on the auricle as a persistent braincomputer interface," Proc Natl Acad Sci USA, vol. 112, no. 13, p. 201424875, March 2015.

[4] D. Looney et al., "An In-The-Ear Platform For Recording Electroencephalogram," Conf Proc IEEE Eng Med Biol Soc, pp. 6882-6885, 2011.

[5] S. L. Kappel and P. Kidmose, "Study of Impedance Spectra for Dry and Wet EarEEG Electrodes," Conf Proc IEEE Eng Med Biol Soc, pp. 3161-3164, 2015.

[6] Y. M. Chi, T. P. Jung, and G. Cauwenberghs, "Dry-Contact and Noncontact Biopotential Electrodes: Methodological Review," IEEE Rev Biomed Eng, vol. 3, pp. 106-119, October 2010.

[7] P. Fiedler et al., "Novel Multipin Electrode Cap System for Dry Electroencephalography," Brain Topogr, vol. 28, no. 5, pp. 647-656, September 2015.

[8] C. T. Lin et al., "Novel dry polymer foam electrodes for long-term EG measurement," IEEE Trans Biomed Eng, vol. 58, no. 5, pp. 1200-1207, May 2011.

[9] P. Fiedler et al., "Multichannel EEG with novel Ti/TiN dry electrodes," Sens Actuators A Phys, vol. 221, no. 1, pp. 139-147, January 2015.

[10] Y. M. Chi et al., "Dry and noncontact EEG sensors for mobile brain-computer interfaces," IEEE Trans Neural Syst Rehabil Eng, vol. 20, no. 2, pp. 228-235, March 2012.

[11] P. Kidmose et al., "A Study of Evoked Potentials From Ear-EEG," IEEE Trans Biomed Eng, vol. 60, no. 10, pp. 2824-2830, October 2013.

[12] S. L. Kappel et al., "A Method for Quantitative Assessment of Artifacts in EEG, and an Empirical Study of Artifacts," Conf Proc IEEE Eng Med Biol Soc, pp. 1686-1690, 2014.

[13] K. B. Mikkelsen et al., "EEG Recorded from the Ear: Characterizing the Ear-EEG Method," Front Neurosci, vol. 9, p. 438, November 2015.

[14] R. D. Meyer et al., "Electrodeposited iridium oxide for neural stimulation and recordingelectrodes," IEEE Trans Neural Syst Rehabil Eng, vol. 9, no. 1, pp. 2-11, March 2001.

[15] S. F. Cogan, "Neural stimulation and recording electrodes," Annu Rev Biomed Eng, vol. 10, pp. 275-309, August 2008.

[16] N. S. Dias et al., "New dry electrodes based on iridium oxide (IrO) for non-invasive biopotential recordings and stimulation," Sens Actuators A Phys, vol. 164, no. 1-2, pp. 28-34, November-December 2010.

[17] J. Augustynski et al., "ESCA study of the state of iridium and oxygen in electrochemically and thermally formed iridium oxide films," J Electroanal Chem Interfacial Electrochem, vol. 160, no. 1-2, pp. 233-248, January 1984.

[18] S. A. M. Marzouk, "Improved electrodeposited iridium oxide pH sensor fabricated on etched titanium substrates," Anal Chem, vol. 75, no. 6, pp. 1258-1266, March 2003.

[19] S. L. Kappel et al., "Physiological artifacts in scalp eeg and ear-eeg," Biomed Eng Online, vol. 16, no. 1, p. 103, August 2017.

[20] A. Delorme and S. Makeig, "EEGLAB: An open source toolbox for analysis of single-trial EEG dynamics including independent component analysis," J Neurosci Methods, vol. 134, no. 1, pp. 9-21, March 2004.

[21] S. L. Kappel et al., "Reference Configurations for Ear-EEG Steady-State Responses," Conf Proc IEEE Eng Med Biol Soc, pp. 5689-5692, 2016.

[22] O. N. Markand, "Alpha Rhythms," J Clin Neurophysiol, vol. 7, no. 2, pp. 163-189, 1990.

[23] C. B. Christensen et al., "Ear-eeg based objective hearing threshold estimation evaluated on normal hearing subjects," IEEE Trans Biomed Eng, August 2017.

[24] R. Näätänen and R. Takegata, "The Mismatch Negativity (MMN)," in The Oxford Handbook of Event-Related Potential Components, 1st ed., S. J. Luck and E. S. Kappenman, Eds. Oxford, Great Britain: Oxford University Press, 2011, ch. 6, pp. 143-157.

[25] R. Näätänen et al., "The mismatch negativity (MMN): Towards the optimal paradigm," Clin Neurophysiol, vol. 115, no. 1, pp. 140-144, January 2004.

The invention claimed is:

1. An electrode for detecting a bioelectrical signal on a skin surface,
said electrode comprising
a skin contact part,
a substrate made of a metal,
a coating comprising iridium oxide,
wherein the coating covers at least part of the skin contact part of the electrode,
wherein the coating comprises a nanostructured surface pattern, and
wherein the nanostructured surface pattern is configured with multiple intersecting ridges to provide a capillary effect, making the part of the skin contact part that is covered by the coating hydrophilic when in contact with the skin surface.

2. The electrode for detecting a bioelectrical signal on a skin surface according to claim 1, wherein the electrode has a base diameter of between 1 and 5 mm.

3. The electrode for detecting a bioelectrical signal on a skin surface according to claim 2, wherein a surface of the skin contact part of the electrode that contacts the skin of a user, is curved with a curvature radius of between 2 and 7 mm.

4. The electrode for detecting a bioelectrical signal on a skin surface according to claim 1, wherein the substrate is made of titanium.

5. The electrode for detecting a bioelectrical signal on a skin surface according to claim 1, wherein the coating comprises additives chosen from the group of tantalum, titanium, platinum, and ruthenium.

6. An ear device for arrangement at an ear of a person, the ear device comprising
at least two electrodes according to claim 1, adapted for detecting a bioelectrical signal from a skin surface when the ear device is arranged at the ear of the person,
an outer surface,
an electronic module comprising power supply means,
wherein the electrodes are provided with a skin contact part arranged on the outer surface of the ear device.

7. The electrode for detecting a bioelectrical signal on a skin surface according to claim 2, wherein the base diameter is between 1.5 and 3.5 mm.

8. The electrode for detecting a bioelectrical signal on a skin surface according to claim 7, wherein the base diameter is between 2.0 and 3.0 mm.

9. The electrode for detecting a bioelectrical signal on a skin surface according to claim 8, wherein the base diameter is 2.6 mm.

10. The electrode for detecting a bioelectrical signal on a skin surface according to claim 3, wherein the curvature radius is between 2.1 and 5 mm.

11. The electrode for detecting a bioelectrical signal on a skin surface according to claim 10, wherein the curvature radius is between 2.2 and 4 mm.

* * * * *